US010816528B2

(12) United States Patent
Yizhack et al.

(10) Patent No.: US 10,816,528 B2
(45) Date of Patent: Oct. 27, 2020

(54) MULTI PARAMETER SWIMMING POOL FLUID ANALYSIS AND REGULATING METHOD AND DEVICE

(71) Applicant: MAYTRONICS LTD., Kibutz Yizrael (IL)

(72) Inventors: Tamir Yizhack, Kiryat Motskin (IL); Shay Peretz, Shimshit (IL); Gil Hilel, Kibbuts Yizrael (IL)

(73) Assignee: MAYTRONICS LTD., Kibbutz Yizrael (IL)

( * ) Notice: Subject to any disclaimer, the term of this patent is extended or adjusted under 35 U.S.C. 154(b) by 338 days.

(21) Appl. No.: 15/513,709

(22) PCT Filed: Sep. 21, 2015

(86) PCT No.: PCT/IB2015/057246
§ 371 (c)(1),
(2) Date: Mar. 23, 2017

(87) PCT Pub. No.: WO2016/046719
PCT Pub. Date: Mar. 31, 2016

(65) Prior Publication Data
US 2017/0248568 A1   Aug. 31, 2017

Related U.S. Application Data

(60) Provisional application No. 62/053,820, filed on Sep. 23, 2014.

(51) Int. Cl.
| | | |
|---|---|---|
| *G01N 33/18* | (2006.01) | |
| *G01J 3/42* | (2006.01) | |
| *G01N 21/00* | (2006.01) | |
| *G01J 3/00* | (2006.01) | |
| *G01N 21/33* | (2006.01) | |
| *G01N 21/3577* | (2014.01) | |

(Continued)

(52) U.S. Cl.
CPC ........... *G01N 33/18* (2013.01); *G01J 3/00* (2013.01); *G01J 3/42* (2013.01); *G01N 21/00* (2013.01);

(Continued)

(58) Field of Classification Search
CPC .... G01N 33/18; G01N 21/00; G01N 21/3577; G01N 2201/129; G01J 3/00; G01J 3/42; C02F 2103/42
See application file for complete search history.

(56) References Cited

U.S. PATENT DOCUMENTS

| | | | | |
|---|---|---|---|---|
| 5,522,225 A | * | 6/1996 | Eskandari | ............... H01L 35/30 |
| | | | | 136/230 |
| 2009/0219513 A1 | * | 9/2009 | Shakespeare | ............. G01J 3/10 |
| | | | | 356/51 |

(Continued)

FOREIGN PATENT DOCUMENTS

| | | |
|---|---|---|
| DE | 19515428 A1 | 11/1996 |
| EP | 0885986 A2 | 12/1998 |

(Continued)

OTHER PUBLICATIONS

International Search Report dated Jan. 7, 2016 for PCT/IB2015/057246, filed Sep. 21, 2015.

(Continued)

*Primary Examiner* — Eric S. McCall
*Assistant Examiner* — Timothy P Graves
(74) *Attorney, Agent, or Firm* — Paul D. Bianco; Gary S. Winer; Fleit Intellectual Property Law

(57) ABSTRACT

There may be provided a system comprising a spectroscopic device; wherein the spectroscopic device is configured to analyze a fluid of a pool.

5 Claims, 22 Drawing Sheets

(51) Int. Cl.
  *G01N 21/359* (2014.01)
  *G01N 21/64* (2006.01)
  *G01N 21/15* (2006.01)
  *E04H 4/16* (2006.01)
  *E04H 4/12* (2006.01)
  *C02F 103/42* (2006.01)

(52) U.S. Cl.
  CPC ............ *G01N 21/15* (2013.01); *G01N 21/33* (2013.01); *G01N 21/359* (2013.01); *G01N 21/3577* (2013.01); *G01N 21/6486* (2013.01); *C02F 2103/42* (2013.01); *C02F 2209/003* (2013.01); *E04H 4/1272* (2013.01); *E04H 4/1654* (2013.01); *G01N 33/1826* (2013.01); *G01N 2021/152* (2013.01); *G01N 2021/154* (2013.01); *G01N 2201/129* (2013.01)

(56) References Cited

U.S. PATENT DOCUMENTS

2010/0292844 A1* 11/2010 Wolf .................. C02F 9/00 700/271
2012/0273351 A1    11/2012 Kraus et al.

FOREIGN PATENT DOCUMENTS

WO    1996/018096 A1    6/1996
WO    2009/068477 A1    6/2009
WO    2012/144955 A1    10/2012

OTHER PUBLICATIONS

Written Opinion for PCT/IB2015/057246, filed Sep. 21, 2015.
Bozena Seredyńska-Sobecka, Colin A. Stedmon, Rasmus Boe-Hansen, Christopher K. Waul, Erik Arvin. Monitoring organic loading to swimming pools by fluorescence excitation-emission matrix with parallel factor analysis (PARAFAC). Article in Water, Research—Mar. 2011.
International Preliminary Report on Patentability dated Mar. 28, 2017 for PCT/IB2015/057246, filed Sep. 21, 2015.
Office Action for Australian Patent Application No. 2015323433 dated Sep. 23, 2019, 3 pages.

* cited by examiner

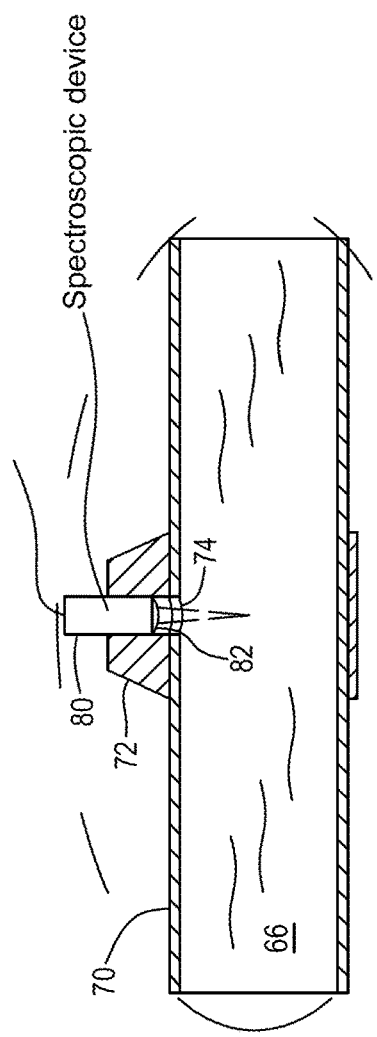
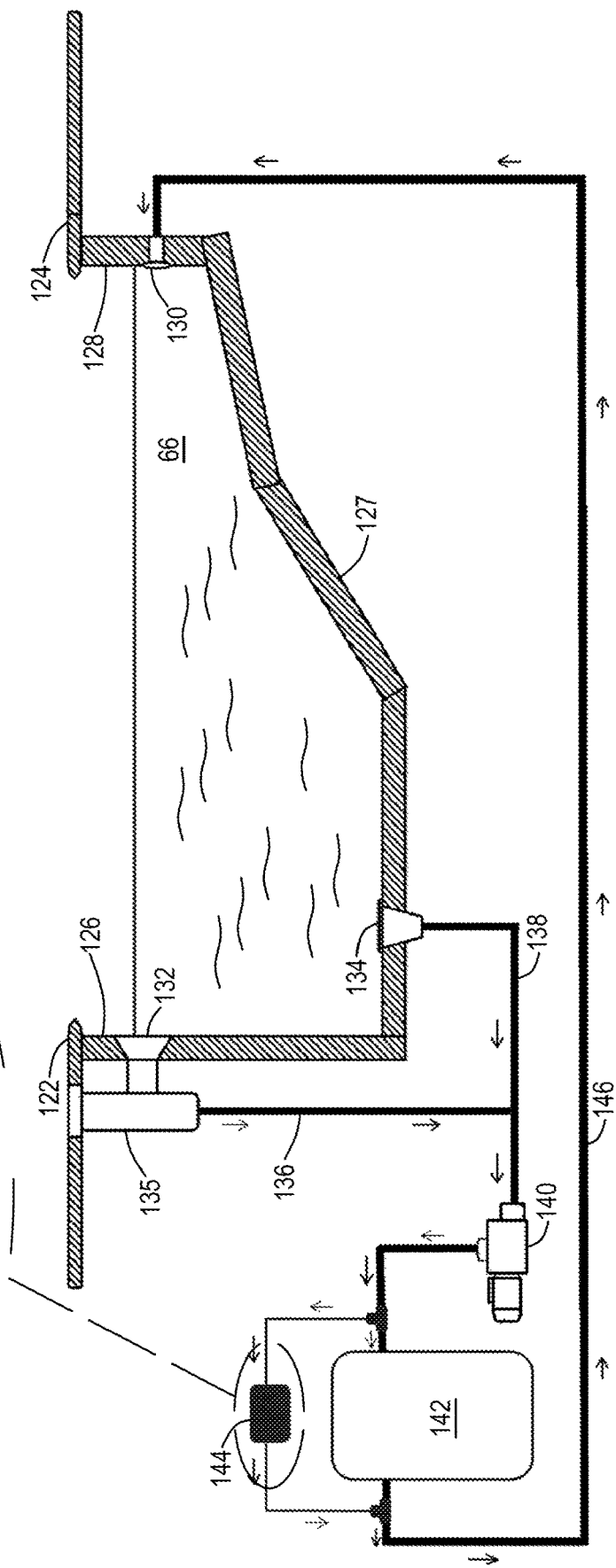

| Component number | Excitation wavelength, nm | Emission wavelength, nm |
|---|---|---|
| 1 | 260, <240, 370 | 520 |
| 2 | 280 | 330 |
| 3 | <240, 330 | 420 |
| 4 | <240 | 370 |
| 5 | <240, 310 | 360 |

Table 3 — Excitation and emission maxima of PARAFAC components found for swimming pool – wastewater samples.

Comparison of the maximum absorption of chloramines and chlorine with previous results

| Compound | This work | | Results of Czech et al. [1] | |
|---|---|---|---|---|
| | $\lambda_{max}$ (nm) | $\epsilon_{max}$ (l mol$^{-1}$ cm$^{-1}$) | $\lambda_{max}$ (nm) | $\epsilon_{max}$ (l mol$^{-1}$ cm$^{-1}$) |
| $Cl_2$ | 331 | 95.7 | 335 | 73 |
| $NH_2Cl$ | 259 | 484.6 | 262 | 423 |
| $NHCl_2$ | 255 | 126.1 | 257 | 135 |
| | 301 | 307.8 | 300 | 293 |
| $NCl_3$ | 262 | 635.4 | 265 | 462 |
| | 344 | 315.0 | 345 | 232 |

FIG. 40

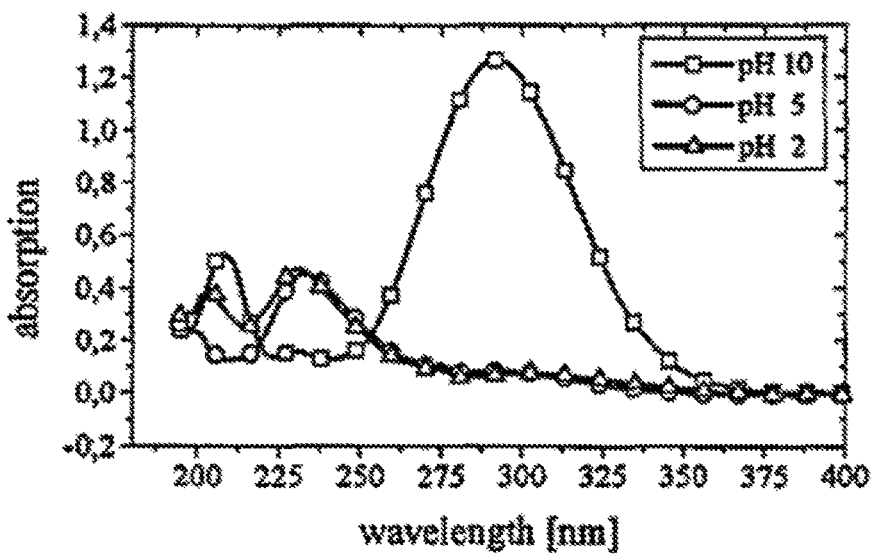

Absorption spectra of 5.76 mg l$^{-1}$ free chlorine as dissolved chlorine ($Cl_2$) at pH 2, as hypochlorous acid (HOCl) at pH 5, and in the form of the hypochlorite ion (OCl$^-$) at pH 10, in an absorption cell (CE) of length 430 mm.

FIG. 41

MULTI PARAMETER SWIMMING POOL FLUID ANALYSIS AND REGULATING METHOD AND DEVICE

RELATED APPLICATIONS

This application claims priority from U.S. provisional patent 62/053,820 filing date 23 Sep. 2014 which is incorporated herein by reference in its entirety.

FIELD OF THE INVENTION

This invention relates to swimming pool fluid analysis and fluid treatment devices.

BACKGROUND OF THE INVENTION

The swimming pool industry is divided into two main classes. The first is the public pool sector that may be defined by pool sizes, volumes of fluid contained and the fact that these may be business or commercially oriented pool owners. It may also be defined by the number of visitors and users to such a pool. i.e.: it is not uncommon to see a small/medium sized public pool with a size of say 12 m×6 m that accommodates a large number of swimmers. This group will comprise of Olympic pools, hotel pools, hostels, caravan park pools, large recreational swimming pools but also smaller community pools that may all need to comply with strict public health regulations governing this sector in their respective countries or municipalities.

The second and possibly the larger pool sector includes the privately owned swimming pools that may usually be smaller in sizes, in their fluid volumes and in number of swimmers. Such pools may not always need to comply with strict fluid quality regulations.

The public pools sector is usually compelled to install expensive fluid quality equipment systems whilst the private sector is not compelled to invest heavily into such equipment but nevertheless, many private pool owners want their pools to be treated to be hygienic and clean.

Fluid treatment in general has the aim of maintaining fluid quality parameters on a continuous basis. This process is based on sampling, sensing, analyzing and appropriately responding to results of analysis.

There is a growing need to provide cost effective pool fluid monitoring systems and methods.

SUMMARY

According to an embodiment of the invention there may be provided system may include a spectroscopic device; wherein the spectroscopic device may be configured to analyze a fluid of a pool. The fluid may be water or any liquid.

The spectroscopic device may be configured to apply at least one spectroscopic technique out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

The spectroscopic device may be configured to apply at least two spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

The spectroscopic device may be configured to apply a majority of spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

The spectroscopic device may be configured to apply (i) at least one spectroscopic technique out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

The applying of one or more spectroscopic technique may include applying a chemometric algorithm.

The applying of one or more spectroscopic technique may include analyzing a wavelength range between one hundred eighty nanometers and two hundred nanometers.

The applying of one or more spectroscopic technique may include analyzing one or more sub-region of a wavelength range between one hundred eighty nanometers and two hundred nanometers.

The applying of one or more spectroscopic technique may include analyzing a wavelength range between two hundred and sixty nanometers and two hundred and eighty nanometers.

The applying of one or more spectroscopic technique may include analyzing one or more sub-region of a wavelength range between two hundred and sixty nanometers and two hundred and eighty nanometers.

The applying of one or more spectroscopic technique may include analyzing a wavelength of two hundred and fifty four nanometers.

The applying of one or more spectroscopic technique may include analyzing a wavelength range between nine hundred eighty nanometers and one thousand nanometers.

The applying of one or more spectroscopic technique may include analyzing one or more sub-region of a wavelength range between nine hundred eighty nanometers and one thousand nanometers.

The applying of one or more spectroscopic technique may include analyzing a wavelength range between one thousand two hundred and sixty nanometers and one thousand two hundred and eighty nanometers.

The applying of one or more spectroscopic technique may include analyzing one or more sub-region of a wavelength range between one thousand two hundred and sixty nanometers and one thousand two hundred and eighty nanometers.

The applying of one or more spectroscopic technique may include analyzing a wavelength of one thousand two hundred and fifty four nanometers.

The applying of one or more spectroscopic technique may include analyzing at least two of the following: (a) a wavelength range between one hundred eighty nanometers and two hundred nanometers, (b) one or more sub-region of a wavelength range between one hundred eighty nanometers and two hundred nanometers, (c) a wavelength range between two hundred and sixty nanometers and two hundred and eighty nanometers, (d) one or more sub-region of a wavelength range between two hundred and sixty nanometers and two hundred and eighty nanometers, (e) a wavelength of two hundred and fifty four nanometers, (f) a wavelength range between nine hundred eighty nanometers and one thousand nanometers, (g) one or more sub-region of a wavelength range between nine hundred eighty nanometers and one thousand nanometers, (h) a wavelength range between one thousand two hundred and sixty nanometers and one thousand two hundred and eighty nanometers, (i) one or more sub-region of a wavelength range between one thousand two hundred and sixty nanometers and one thousand two hundred and eighty nanometers, and (j) a wavelength of one thousand two hundred and fifty four nanometers.

The applying of one or more spectroscopic technique may include applying the one or more spectroscopic technique at a resolution of one nanometer.

The applying of one or more spectroscopic technique may include applying the one or more spectroscopic technique at a resolution that does not exceed one nanometer.

The applying of one or more spectroscopic technique may include applying the one or more spectroscopic technique at a resolution that exceeds one nanometer.

The system may include at least one additional sensor that is not a spectroscopic sensor.

The at least one additional device may be selected from a group consisting of (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, (m) a Salinity sensor.

The system may include multiple additional sensors that are not spectroscopic sensors and are selected from a group consisting of (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, and (m) a Salinity sensor.

The system may include a self-cleaning mechanism for cleaning a spectroscopic sensor of the spectroscopic device.

The system may include a self-cleaning mechanism for cleaning a spectroscopic sensor of the spectroscopic device.

The system may include a self-cleaning mechanism for cleaning one or more additional sensor that is not a spectroscopic sensor.

The self-cleaning mechanism may include an acoustic vibrator.

The self-cleaning mechanism may include a mechanical cleaning element that may be configured to clean an optical element of a sensor of the system.

The mechanical cleaning element may include at least one out of (a) a brush, (b) a rag, (c) a wiper, and (d) a Teflon sphere.

The system may be a pool cleaning robot.

The spectroscopic device may include a spectroscopic sensor that extends outside a housing of the pool cleaning robot.

The spectroscopic device may include a spectroscopic sensor that is positioned within a housing of the pool cleaning robot.

The spectroscopic device may include a spectroscopic sensor that is positioned at a top portion of the pool cleaning robot.

The spectroscopic device may include a spectroscopic sensor that is positioned at a bottom portion of the pool cleaning robot.

The spectroscopic device may include a spectroscopic sensor that is positioned at a rear portion of the pool cleaning robot.

The spectroscopic device may include a spectroscopic sensor that is positioned at a left portion of the pool cleaning robot.

The system may include a floating unit and a submerged unit.

The spectroscopic device may be configured to receive fluid through an opening of the submerged unit.

The spectroscopic device may include photovoltaic cells for energizing the system.

The system may include an interface for coupling the system to the pool.

The interface may be configured to may include a detachable coupling of the system to the pool.

The system that does not may include an interface for coupling the system to the pool.

The system is may be skimmer.

The skimmer may have a skimmer opening for receiving fluid from the pool, wherein the skimmer opening is positioned at a sidewall of the pool.

The system may include an interface for coupling the system to a skimmer.

The system may include an opening for receiving fluid that entered a skimmer.

The skimmer may have a skimmer opening for receiving fluid from the pool, wherein the skimmer opening is positioned at a sidewall of the pool.

The system may be a pool filtering system that may be configured to filter the fluid of the pool.

The system may include an interface for coupling the system to a pool filtering system that may be configured to filter the fluid of the pool.

The system may include an opening for receiving fluid that entered a pool filtering system that may be configured to filter the fluid of the pool.

The spectroscopic device may include a pipe, optics that are configured to direct electromagnetic radiation through an opening formed in the pipe and to receive electromagnetic radiation from the fluid.

The optics may be positioned within a saddle that interfaces the pipe.

The spectroscopic device may include (a) optics that are configured to direct electromagnetic radiation through an opening formed in a pipe and to receive electromagnetic radiation from the fluid, and (b) an interface for attaching the optics to a the pipe.

The spectroscopic device may be calibration free.

The spectroscopic device may be reagent free.

The system further may include a transceiver.

The system may include a wireless transceiver.

The system may include a short range transceiver.

According to an embodiment of the invention there may be provided a method for analyzing a fluid of a pool, the method comprises analyzing the pool fluid by a spectroscopic device.

The method may include applying at least one spectroscopic technique out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

The method may include receiving one or more samples of a fluid of a pool.

The method may include analyzing the fluid of a pool—and especially analyzing the one or more samples of the fluid of the pool by a spectroscopic device.

The method may include applying any number of spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

The method may include applying a chemometric algorithm.

The method may include analyzing at least two of the following: (a) a wavelength range between one hundred eighty nanometers and two hundred nanometers, (b) one or more sub-region of a wavelength range between one hundred eighty nanometers and two hundred nanometers, (c) a wavelength range between two hundred and sixty nanometers and two hundred and eighty nanometers, (d) one or more sub-region of a wavelength range between two hundred and sixty nanometers and two hundred and eighty nanometers, (e) a wavelength of two hundred and fifty four nanometers, (f) a wavelength range between nine hundred eighty nanometers and one thousand nanometers, (g) one or more sub-region of a wavelength range between nine hundred eighty nanometers and one thousand nanometers, (h) a wavelength range between one thousand two hundred and sixty nanometers and one thousand two hundred and eighty nanometers, (i) one or more sub-region of a wavelength range between one thousand two hundred and sixty nanometers and one thousand two hundred and eighty nanometers, and (j) a wavelength of one thousand two hundred and fifty four nanometers.

The method may include applying the one or more spectroscopic technique at a resolution of one nanometer, or a resolution that does not exceed one nanometer or a resolution that exceeds one nanometer.

The method may include performing an additional analysis of the fluid of the pool. The analysis can be performed on the sampled obtained during step 510 or on other samples. The additional analysis is not a spectroscopic analysis.

The method may include performing the additional analysis by at least one additional sensor out of (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, (m) a Salinity sensor.

The method may include self-cleaning the spectroscopic device and/or one or more additional sensor.

The self-cleaning may involve using a self-cleaning mechanism such as but not limited to an acoustic vibrator, a mechanical cleaning element.

The method may include can be executed by a pool cleaning robot, by a system that includes a floating unit and a submerged unit, by a system that is connected to the sidewall of the pool, by a skimmer, by a system that is included within a skimmer, by a system that receives fluid from a pool filtering system, by the pool filtering system.

The method may include directing, by optics, electromagnetic radiation through an opening formed in a pipe and receiving electromagnetic radiation from the fluid.

Any combination of any component illustrated in any figure and.or referred to in the specification can be provided.

According to an embodiment of the invention the fluid of the pool may be analyzed by multiple spectroscopic devices. Different spectroscopic devices may analyze the same spectrum or may analyze different spectrums.

BRIEF DESCRIPTION OF THE DRAWINGS

In order to understand the invention and to see how it may be carried out in practice, a preferred embodiment will now be described, by way of non-limiting example only, with reference to the accompanying drawings.

FIG. 3 illustrates a spectroscopic device that is embedded in a pool filtering system according to an embodiment of the invention;

FIG. 4 is a cross section of a pipe and a spectroscopic device that is configured to analyze the fluid that flows through the pipe according to an embodiment of the invention;

FIGS. 16-41 illustrate spectroscopic analysis results according to an embodiment of the invention.

DETAILED DESCRIPTION OF THE DRAWINGS

Figure 1:
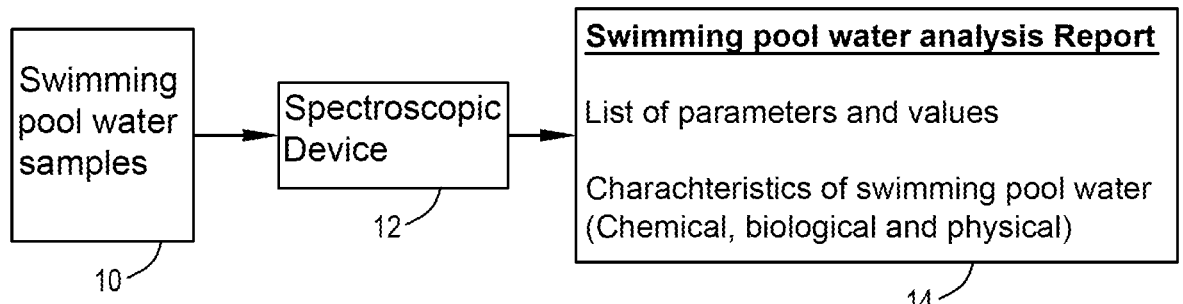
FIG. 1 is a schematic of a spectroscopic device and an analysis report according to an embodiment of the invention.

There is provided a system and method for performing spectroscopy of pool fluid that may use a micro total analysis system (MicroTAS) that is based on the employment of a 'micro' spectroscope or spectrometer to analyze and/or regulate pool fluid quality. A non-limiting example of a micro spectroscope (also referred to as a spectroscopic device) is the SCiO of consumer physics Inc.

The term pool means any vessel that is capable of containing fluid.

It can be established that the present invention relates to a miniaturized integrated spectroscopic sensor, with integrated sensed signal conditioning, signal exchange, and integration into a compact spectroscopic device for the measurement of solution and solvent-based chemistries. With adaptation, the spectroscopic device can be configured for solids or gases, but liquids are the preferred implementation. The sensed information is converted into meaningful information in the form of concentrations of specified species and for the composition or properties of mixtures and composite materials.

The present invention uses a miniaturized, low cost spectral sensing spectroscopic device, a major advancement in measurement opportunity over the current state of the art within the swimming pool industry, and overcomes issues related to size or space occupied in the laboratory, or the size of a portable spectrometer. Each spectroscopic device is intended to provide the functionality of a normal spectrometer or spectral analyzer, but at reduced cost, and with a significantly reduced size for the total package.

Specifically, the invention relates to a method of integrating the spectroscope or the spectrometer with the filtering system of the swimming pool. Such a system comprises, in very general terms, of an external closed loop system whereby fluid from the pool is pumped, by means of a pump, into a filtering spectroscopic device that returns the filtered fluid back to the pool.

According to the preferred embodiment of the invention there may be provided a spectroscopic multi-parameter swimming pool fluid-sensing spectroscopic device for fluid analysis and transmission of said parameter results to a peripheral computing spectroscopic device whereby the computing spectroscopic device may further act to physically regulate the swimming pool fluid treatment according to the analyzed results.

According to the preferred embodiment of the invention there may be provided at least one spectroscopic sensing spectroscopic device (hereinafter: the spectroscopic device) for determining properties of a fluid in real-time, said spectroscopic device comprising:
a. An integrated energy source and an integrated spectroscopic sensing detector package having a spectroscopic sensing detector.
b. A sample window or cell, disposed adjacent to said package, and dimensionally designed to match an active area of the spectroscopic sensing detector.
c. Integrated electronics coupled to said package for providing energy for said source and for receiving a signal generated by said spectroscopic sensor in response to energy coupled to said detector by said sample window or cell, said integrated electronics providing direct output of sample properties of said sample;
d. Said integrated electronics having on-board computer processing with a microcomputer or digital signal processor, and;
e. Said integrated electronics having on-board data communications including output to at least one of a visual display, communications of results to a process monitoring computer, and an option for wireless communications to a network.
f. Using analysis results to activate a regulating fluid treatment system either automatically or on command of a user.
g. The spectroscopic sensing spectroscopic device may act without contact or sampling of the fluid.

The spectroscopic device may be based on Raman, ultraviolet (UV)/Vis (visual light), Fluorescence, infrared (IR)/Near-IR spectroscopy or any other spectroscopic sensing methodology.

The said on-board computer processing may include a memory for data, calibration coefficients, methods and results.

The communication of results to a process monitoring computer control or automation system is used to command operations of a variety of spectroscopic device s to better process and treat the fluid under analysis.

The results may include data on levels of Chlorine, Total Dissolved Salts (TDS), Turbidity, Phosphates, Temperature, pH, ORP, Flow Rate, Algae, Bacteria, circulated fluid flow rates in the filtering system, and any or all other physical, chemical and biological parameters or species.

The communication of results may be interpreted for the goal of stabilizing and maintaining pool fluid quality and be sent to an automated regulation system of fluid that dispenses chemical compounds into the pool system.

The sample window or cell allows for continuous monitoring of a continuous stream of fluid circulating in a pool.

The sample window or cell surface allows for self-cleaning.

The self-cleaning is done by means of acoustic vibrations, mechanical swiping, etc. that may be connected and activated by the spectroscopic device.

The spectroscopic device may comprise of a kit that includes a pipe saddle and fittings to attach the spectroscopic device to a swimming pool filtering system piping.

In another embodiment, the spectroscopic device may be installed or connected to swimming pool equipment.

The spectroscopic device may be installed or connected to swimming pool equipment that is an automatic pool cleaning apparatus.

The spectroscopic device of this first embodiment may be a fluidproof spectroscopic device that may be battery operated using replaceable rechargeable batteries.

The said swimming pool apparatus has the ability to receive data being wirelessly transmitted from the spectrometer that is located inside its hollow body.

The transmission may be performed wirelessly underwater by means of a Bluetooth® electronic card that will emit data to a PCB or CPU control unit inside the pool cleaner control box or a central motor unit.

The data may be further sent by means of the pool cleaner electrical cable to an external unit such as the pool cleaner's power supply.

The power supply may be able to emit the data—by means of Bluetooth® or a Wi-Fi from the spectroscopic device—to any receiving communication utility: a home computer, smartphone and the like.

The spectroscopic device of this first embodiment may also be wired to the said PCB or CPU control unit inside the pool cleaner control box or a central motor unit.

In yet another, second embodiment, the spectroscopic device may be installed or connected to swimming pool equipment that is a skimmer.

The spectroscopic device of this second embodiment may be a waterproof spectroscopic device that is battery operated using replaceable batteries.

The spectroscopic device of this second embodiment will be connected or attached to the inside area of the skimmer to so that the light beam be directed at the fluid to register fluid quality parameters.

The spectroscopic device of this second embodiment will be connected or attached to the inside area of the skimmer may be able to wirelessly communicate by means of Bluetooth® or Wi-Fi to any receiving communication utility such as a smartphone.

All communications of both first and second embodiments are intended to advise the end user about the state of the swimming pool fluid.

All communications of the preferred embodiment are meant to advise the end user about the state of the swimming pool fluid and automatically—or subject to a manual command—proceed to activate the dosing equipment to regulate the chemistry composition of the pool fluid.

The spectroscopic devices of both the first and second embodiments may be removable The spectroscopic devices of both the first and second embodiments may be used as hand held spectroscopic devices.

The term 'spectroscopy' or 'spectroscopic' means any process of analyzing the interaction between radiated energy and matter. The term spectrometer means a device which provides qualitative and quantitative identification of materials based on spectroscopic analysis.

FIG. 1 is a schematic of a spectroscopic device 12 and an analysis report according to an embodiment of the invention.

The spectroscopic device 12 receives sampled of swimming pool fluid 10, analyzes the fluid and outputs a swimming pool analysis report 14.

According to an embodiment of the invention the spectroscopic device may be configured to analyze a fluid of a pool.

According to an embodiment of the invention the spectroscopic device may be configured to apply any number of spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

According to an embodiment of the invention the spectroscopic device may be configured to apply any combination of spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

According to an embodiment of the invention an applying of one or more spectroscopic techniques (such as the spectroscopic techniques mentioned above) may include applying a chemometric algorithm.

Chemometric (see wikipedia.org) is the science of extracting information from chemical systems by data-driven means. Chemometric is inherently interdisciplinary, using methods frequently employed in core data-analytic disciplines such as multivariate statistics, applied mathematics, and computer science, in order to address problems in chemistry, biochemistry, medicine, biology and chemical engineering. In this way, it mirrors other interdisciplinary fields, such as psychometrics and econometrics.

Chemometric is applied to solve both descriptive and predictive problems in experimental natural sciences, especially in chemistry. In descriptive applications, properties of chemical systems are modeled with the intent of learning the underlying relationships and structure of the system (i.e., model understanding and identification). In predictive applications, properties of chemical systems are modeled with the intent of predicting new properties or behavior of interest. In both cases, the datasets can be small but are often very large and highly complex, involving hundreds to thousands of variables, and hundreds to thousands of cases or observations.

Chemometric techniques are particularly heavily used in analytical chemistry and metabolomics, and the development of improved chemometric methods of analysis also continues to advance the state of the art in analytical instrumentation and methodology. It is an application driven discipline, and thus while the standard chemometric methodologies are very widely used industrially, academic groups are dedicated to the continued development of chemometric theory, method and application development.

Chemometric may include applying one or more multivariate calibration techniques, supervised multivariate classification techniques, unsupervised classification techniques, multivariate curve resolution, multivariate statistical process control (MSPC), and multiway methods.

The inventors found that applying a chemometric algorithm may improve the analysis of the fluid. For example—when using NIR spectroscopy the chemometric algorithm can significantly improve the analysis.

The inventors found that a single spectrometric method may provide some useful information, but that it is likely that more than one method will have to be applied.

The inventors found that that Ultra-Violet absorption spectroscopy and Ultra-Violet fluorescence spectroscopy are good candidates for monitoring swimming pool fluid.

The inventors found that SERS (surface enhanced Raman spectroscopy) is another good candidate for monitoring swimming pool fluid.

The inventors found that IR spectroscopy with a comparison to a reference may be a good candidate for monitoring swimming pool fluid.

The inventors found that spectroscopic data may provide more detailed information than non-spectroscopic fluid analysis methods. For example, information of some organic contaminants and on biological species might be extracted from fluorescence data obtained by fluorescence spectroscopy. Non-limiting examples may include specific, real time digital data about urine or turbidity levels in a swimming pool that are practically impossible to automatically assess with present day equipment.

The inventors found that having one or more additional sensors (that are not spectroscopy based sensor) my further improve the quality of the fluid analysis.

According to an embodiment of the invention an applying of one or more spectroscopic technique may include analyzing one or more of the following: (a) a wavelength range between one hundred eighty nanometers and two hundred nanometers, (b) one or more sub-region of a wavelength range between one hundred eighty nanometers and two hundred nanometers, (c) a wavelength range between two hundred and sixty nanometers and two hundred and eighty nanometers, (d) one or more sub-region of a wavelength range between two hundred and sixty nanometers and two hundred and eighty nanometers, (e) a wavelength of two hundred and fifty four nanometers, (f) a wavelength range between nine hundred eighty nanometers and one thousand nanometers, (g) one or more sub-region of a wavelength range between nine hundred eighty nanometers and one thousand nanometers, (h) a wavelength range between one thousand two hundred and sixty nanometers and one thousand two hundred and eighty nanometers, (i) one or more sub-region of a wavelength range between one thousand two hundred and sixty nanometers and one thousand two hundred and eighty nanometers, and (j) a wavelength of one thousand two hundred and fifty four nanometers.

A sub-region of a wavelength range may include one or more wavelengths. A sub-region may include a continuous sequence of wavelengths within a wavelength range, a non-continuous combination of frequencies within the wavelength range or a combination thereof.

According to an embodiment of the invention an applying of one or more spectroscopic technique may include analyzing one or more wavelengths ranges and/or one or wavelength sub-regions that substantially equal the mentioned above wavelengths ranges and/or one or wavelength sub-regions. The term "substantially" means that a predefined deviation is allowed. The predefined deviation may be, for example, up to thirty nanometers, up to twenty percent, and the like.

For example, referring the wavelength range between one hundred eighty nanometers and two hundred nanometers—a wavelength range that substantially equals said wavelength range may (a) range between one hundred fifty nanometers till two hundred and thirty nanometers, or (b) range between one hundred eighty nanometers till two hundred and thirty nanometers, or (c) range between one hundred fifty nanometers till two hundred nanometers, and the like.

According to an embodiment of the invention the spectroscopic device may analyze one or few wavelength ranges or sub-ranges—instead of scanning a large wavelength range- and this dramatically reduces the cost of the spectroscopic device. This also allows using optical components (such as filters, lenses and lasers) that are fitted to a relatively narrowband and thus are cheaper than broadband compliant optical components.

Alternatively—the illumination and/or collection can involve broadband illumination and/or collection.

According to an embodiment of the invention an applying of one or more spectroscopic technique may include applying the one or more spectroscopic technique at a resolution of one nanometer, at a resolution that does not exceed one nanometer or at a resolution that exceeds one nanometer (nm).

Non-limiting examples of resolution may include 0.1 nm, 0.2 nm, 0.3 nm, 0.4 nm, 0.5 nm, 2 nm, 3 nm, 4 nm, 5 nm, 6 nm, 7 nm, 8 nm, 9 nm, 10 nm, and the like. Etc.).

According to an embodiment of the invention the system may include one or more additional sensors—an additional sensor is assumed to differ from a spectroscopic sensor.

According to an embodiment of the invention the at least one additional device may include at least one (or any combination of) of the following sensors: (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, (m) a Salinity sensor.

According to an embodiment of the invention the system may include a self-cleaning mechanism for cleaning a spectroscopic sensor of the spectroscopic device.

When the system includes one or more additional sensors, that system may also include self-cleaning mechanism for cleaning the one or more additional sensors (that are not a spectroscopic sensor).

The cleaning mechanism may be at least one out of (a) and acoustic vibrator, (b) a mechanical cleaning element that may be configured to clean an optical element of a sensor of the system, the mechanical cleaning element may be, for example, (a) a brush, (b) a rag, (c) a wiper, and (d) a Teflon sphere.

According to an embodiment of the spectroscopic device, it may include a swimming pool filtering system pipe or conduit, optics that are configured to direct electromagnetic radiation through an opening formed in the pipe and to receive electromagnetic radiation from the fluid.

According to an embodiment of the invention the optics are positioned within a saddle that interfaces and is secured to the said pipe.

The said spectroscopic device and its saddle may be part of a kit that may be installed by an end user onto the said pipe or conduit.

According to an embodiment of the invention the spectroscopic device is calibration free.

According to an embodiment of the invention the spectroscopic device is reagent free.

According to an embodiment of the invention the spectroscopic device may be configured to provide comprehensive analysis information (chemically, biologically and physically) accurately, reliably and continuously. The spectroscopic device may perform the spectroscopic analysis without using reagents, in a robust manner, without any calibration, be inexpensive, and according to the comprehensive measurement and analysis enables reaching of intelligent conclusions and as a result enables effective treatment or other remedies to the swimming pool fluid The spectroscopic device may provide a comprehensive swimming pool fluid analysis that may include a chemical analysis (chemical compound such as: free Chlorine, combine Chlorine, Calcium, Cyanuric-acid, etc.), a biological analysis (organic materials such as: sweat, urine, plants, micro-organisms, etc.) and a physical analysis (temperature, pressure, turbidity, etc.).

This analysis may improve any fluid treatment process by reducing chemicals consumption, reduce fluid consumption, reduce energy consumption, reduce amount of particles in fluid, reduce skin and/or eye irritation, reduce fluid hazards, and extend the lifespan of the swimming pool filtering system.

Figure 2:
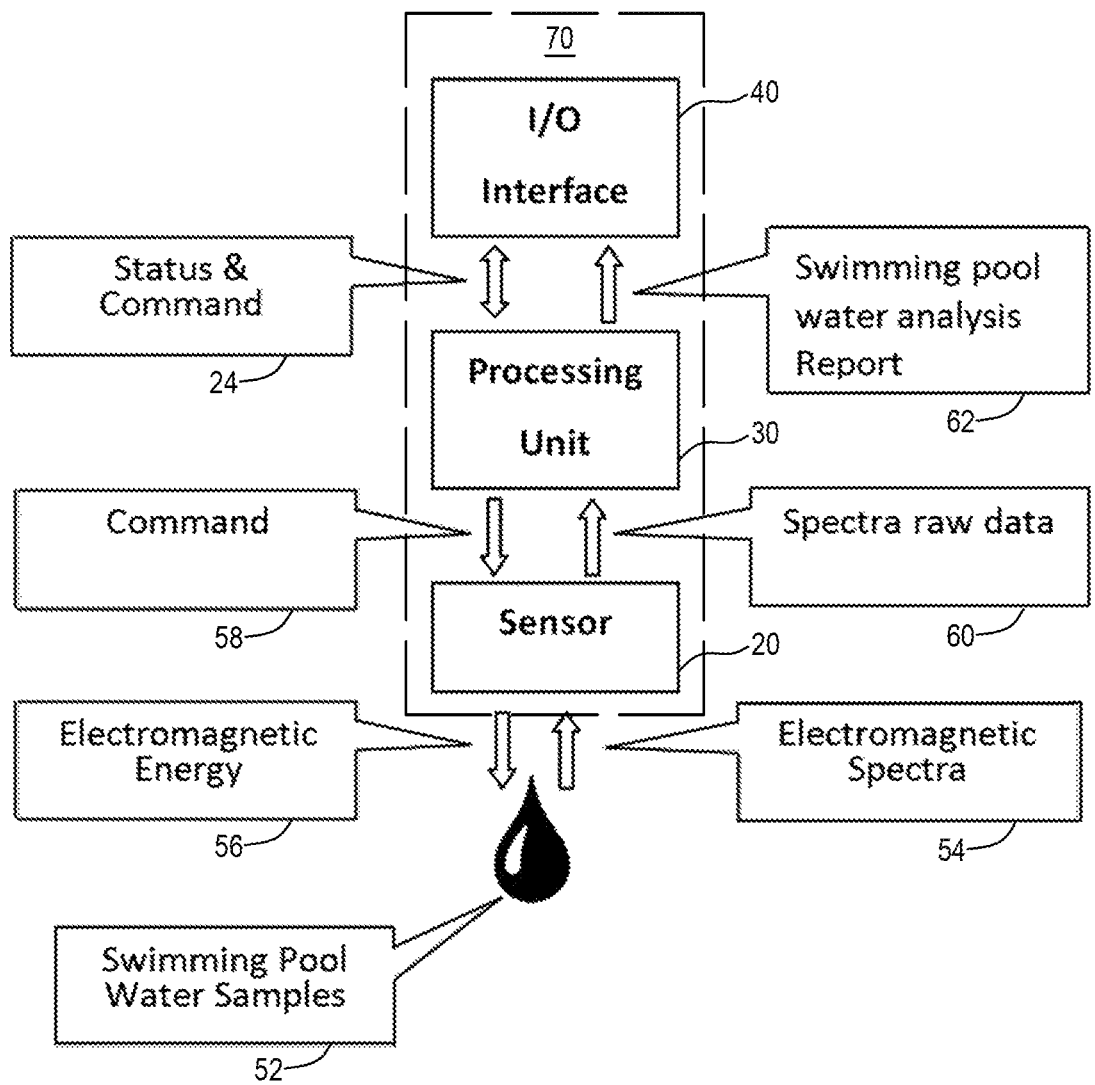
FIG. 2 illustrates an analysis process according to an embodiment of the invention.

FIG. 2 illustrates an analysis process according to an embodiment of the invention.

The spectroscopic device 70 includes sensor 20, processing unit 30 and input output (IO) interface 40.

The sensor 20 may include optics for directing electromagnetic radiation 56 towards a pool fluid sample 52 and for receiving electromagnetic spectra 54 from the pool fluid samples—resulting from the illumination of the pool fluid samples 52 by electromagnetic radiation 56. The electromagnetic spectra 54 can result from absorbance and/or fluorescence.

The sensor 20 generates spectra raw data (such as intensity or power per wavelength) 60 that is sent to processing unit 30. Processing unit 30 processes the spectra raw data (for example by applying a chemometric algorithm) to provide the swimming pool analysis report 14 to the IO interface 40.

The swimming pool analysis report 14 may be any arrangement of information that represents one or more quality, parameters or characteristics of the fluid.

IO interface 40 may transmit (wirelessly or non-wirelessly) the swimming pool analysis report 14 to another device, may display the swimming pool analysis report 14 to a user, be connected to an alarm or other warning device and the like. IO interface 40 may send status and command 24 to the processing unit 30 that may send commands to the sensor 20.

The spectra raw data can be processed (by processing unit 30) by applying a chemometric algorithm and translated into a list of parameter values that represent the compounds present in the fluid.

The spectra raw data can be used to determine kinetics of fluid chemistry and make predictions of fluid quality and treatment required not otherwise possible. Frequency of spectra and kinetic determinations can be generated over minutes, hours, days or weeks (see below).

In FIGS. 3-10 any reference to a spectroscopic device may be regarded as a reference to a sensor of the spectroscopic device. Other components of the spectroscopic device can be located elsewhere—and receive spectra raw data from the sensor via a communication link.

FIG. 3 illustrates spectroscopic device 144 that is a part of a pool filtering system according to an embodiment of the invention.

The pool filtering system is configured to filter the fluid of a pool that includes bottom 127, right sidewall 128, left sidewall 126 and contains fluid 66. Fluid is sucked through skimmer opening 132 (formed in left sidewall 126) of skimmer 135 and through drain 134 (formed in bottom 127) propagates through pipes 136 and 138 towards pump 140 and is then sent to filter 142 and (in parallel) to spectroscopic device 144.

Thus, spectroscopic device 144 may analyze fluid that passes through the pool filtering system. The filtered fluid and the analyzed fluid are fed back through pipes 146 to an outlet or jet 130 formed in right sidewall 128. FIG. 3 also illustrates the upper surface/edge or pool deck 122 and 124 that surrounds the pool.

It is noted that the spectroscopic device 144 may positioned in various other locations—for example it may be positioned within skimmer 135, in proximity to drain 134, may sample fluid flowing through each one of pipes 136 and 138, may precede pump 140, may sample fluid between pump 140 and filter 142, or at the input of 132 and the like.

It is further noted that the fluid filtering system may differ from the fluid filtering system of FIG. 3. For example, the fluid filtering system may receive fluid via only one of skimmer 135 and drain 138, may not include a skimmer, may include more than two openings for receiving pool fluid, may be positioned above the pool, and the like.

FIG. 4 is a cross section of a pipe 70 and a spectroscopic device 80 that is configured to analyze the fluid that flows through the pipe according to an embodiment of the invention.

Fluid 66 that flows through pipe 70 is illuminated by electromagnetic spectra that propagate through opening 74 within pipe 70. In FIG. 4 the electromagnetic spectra 54 from fluid 66 passes through the opening 74 although the electromagnetic spectra may pass through another opening (not shown). FIG. 4 illustrates a lens 82 of the spectroscopic device 80. It is noted that the spectroscopic device 80 may include additional optical components.

Opening 74 may be a transparent or partially transparent window or cover.

Spectroscopic device 80 of FIG. 4 may include a processing unit and/or an IO interface (see FIG. 2)—although the processing device and/or the IO interface may be positioned elsewhere.

In FIG. 4 the spectroscopic device 80 is connected to pipe 70 via a saddle 72. It is noted that spectroscopic device 80 may be positioned within pipe 70 or attached to the pipe 70 is any other manner.

Figure 5:
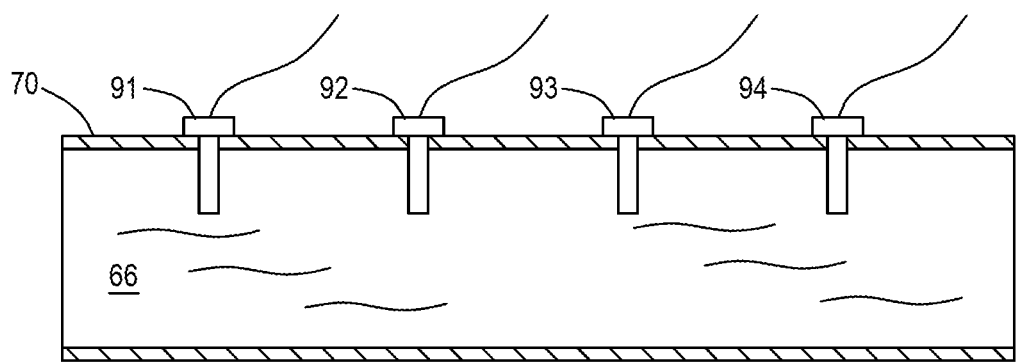
FIG. 5 is a cross section of a pipe and a multiple additional sensors that are configured to sense various elements within the fluid that flows through the pipe according to an embodiment of the invention.

FIG. 5 is a cross section of a pipe 70 and a multiple additional sensors 91, 92, 93 and 94 that are configured to sense various elements within the fluid that flows through the pipe according to an embodiment of the invention.

There may be one, two, three, four or more than four additional sensors. The one or more additional sensors may be positioned close (within few centimeters) from spectroscopic device 80 or may be spaced apart from spectroscopic device 80.

The one or more additional sensor may be selected out of (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, (m) a Salinity sensor.

Figure 6:
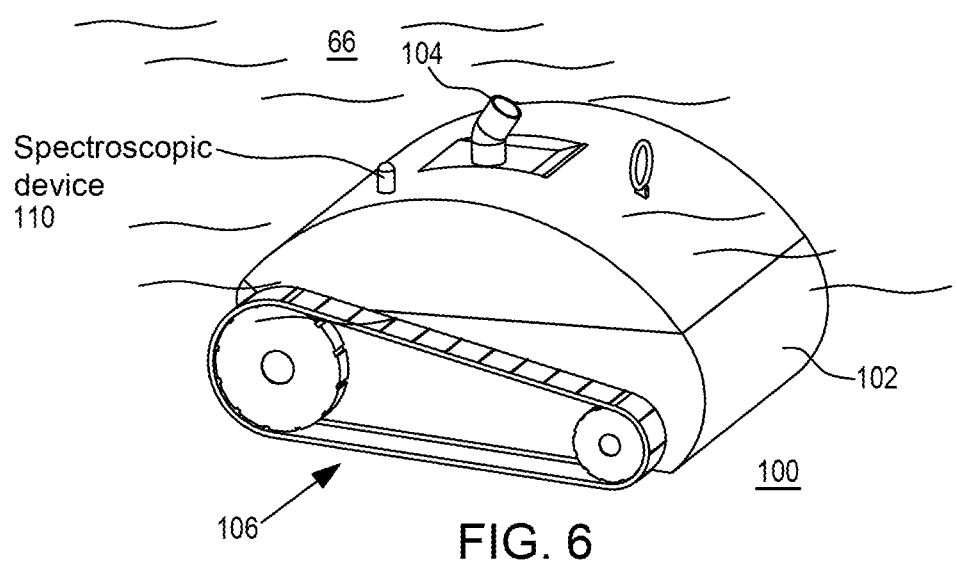
FIG. 6 illustrates a pool cleaning robot that comprises a spectroscopic device according to an embodiment of the invention.

FIG. 6 illustrates a pool cleaning robot 100 that includes a spectroscopic device according to an embodiment of the invention.

FIG. 6 illustrates that the sensor 110 of the spectroscopic device extends outside housing 102 of the pool cleaning robot 100.

Sensor 110 may be positioned at any position in relation to the housing 102—at the upper portion, at the lower portion, at a right part of housing 102, at the left portion of housing 102 and the like.

The sensor 110 may be positioned within housing and preferably before a filtering unit (not shown) of the pool cleaning robot 100.

The pool cleaning robot 100 may include a propulsion system that may include a motor, gear and interfacing elements such as tracks and rotating wheels collectively denoted 106 in FIG. 6), wheels of a trackless pool cleaning robot, and the like. The pool cleaning robot also includes a filtering unit that may receive fluid through an inlet and output filtered fluid through an outlet (such as outlet 104 of FIG. 6).

The pool cleaning robot 100 may perform the spectroscopic analysis while being static, during movement, during filtering periods in which the pool cleaning robot filters the fluid of the pool, outside a filtering period, in a partially overlapping manner with the filtering process, and the like.

The pool cleaning robot 100 may perform multiple spectroscopic analysis iterations and assign time stamps/location information to the different spectroscopic analysis iterations. This may enable to map the outcome of the different spectroscopic analysis iterations to different locations within the pool and/or to different times.

For example, the pool cleaning robot 100 may compare results of spectroscopic analysis iteration before a filtering process to results of a spectroscopic analysis iteration conducted after a filtering process to evaluate the filtering process.

Yet for another example—the pool cleaning robot may be configured to provide a map of spectroscopic analysis iteration results and locations within the pool thereby allowing a pool owner to detect problems related to different regions of the pool.

Figure 7:
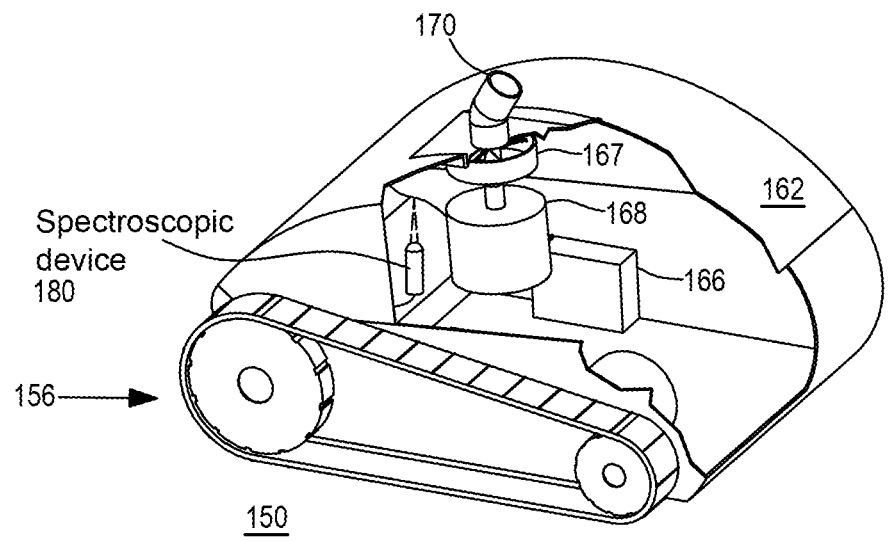
FIG. 7 illustrates a pool cleaning robot that comprises a spectroscopic device according to an embodiment of the invention.

FIG. 7 illustrates that the sensor 180 of the spectroscopic device is included within housing 162 of pool cleaning robot 150, according to an embodiment of the invention.

In FIG. 7 the pool cleaning robot 150 is illustrated as including propulsion unit 156, impeller 167, pump motor 168 for rotating the impeller, and controller 166.

Figure 8:
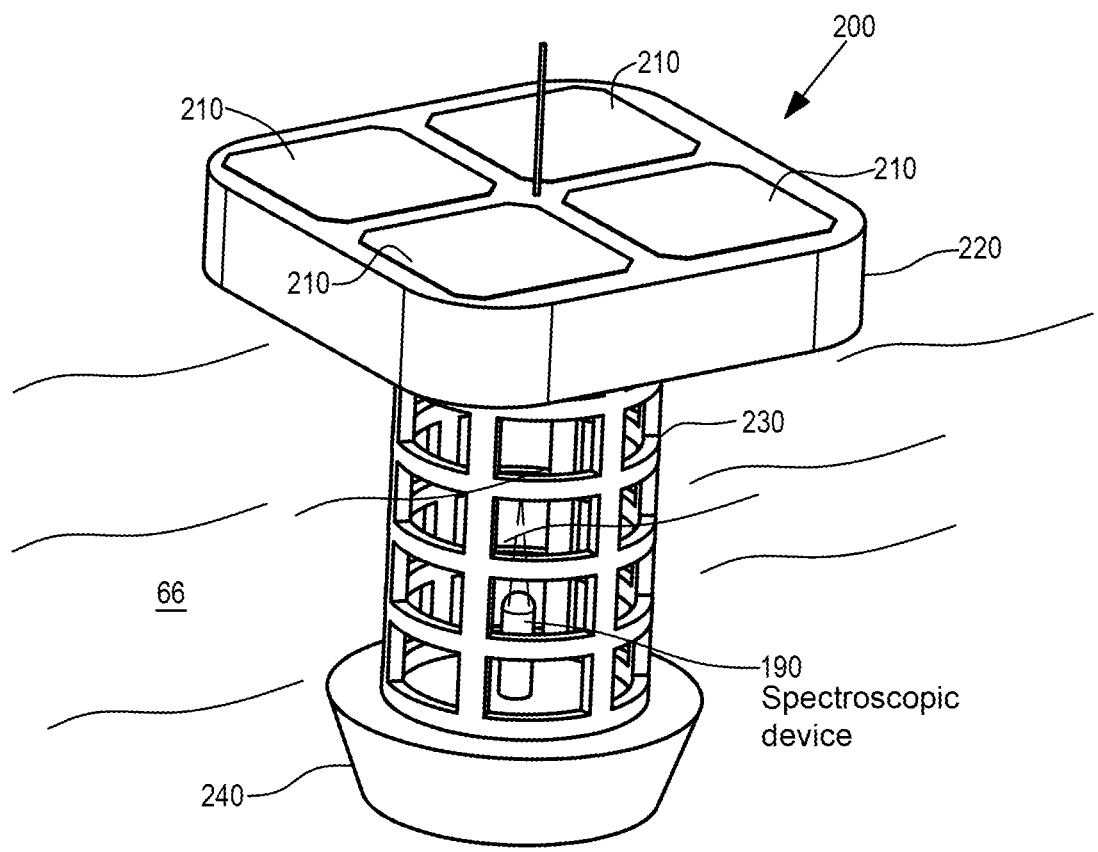
FIG. 8 illustrates a system that includes a floating unit, a submerged unit and a spectroscopic device according to an embodiment of the invention.

FIG. 8 illustrates a system 200 that includes a floating unit 220, a submerged unit and a spectroscopic device 190 according to an embodiment of the invention.

System 200 includes a submerged unit that includes grid 230 and a bottom 240. The grid 230 and the bottom 240 are submerged when the system 200 is placed in a pool. The spectroscopic device 190 may analyze fluid that flow through the apertures of grid 230.

The floating unit 220 includes photovoltaic cells 210 (arranged in one or more panels) for supplying power to system 200. Additionally or alternatively, system 200 may include a battery or any other power supply and a control PCB.

It is further noted that part of the grid 230 may be above the fluid level and include a PCB communications antenna System 200 may float freely in the pool. It may or may not be attached to the pool or to any other structural element and may contain an onboard chemical compound dispenser facility such as a flocculent (not shown).

Figure 9:
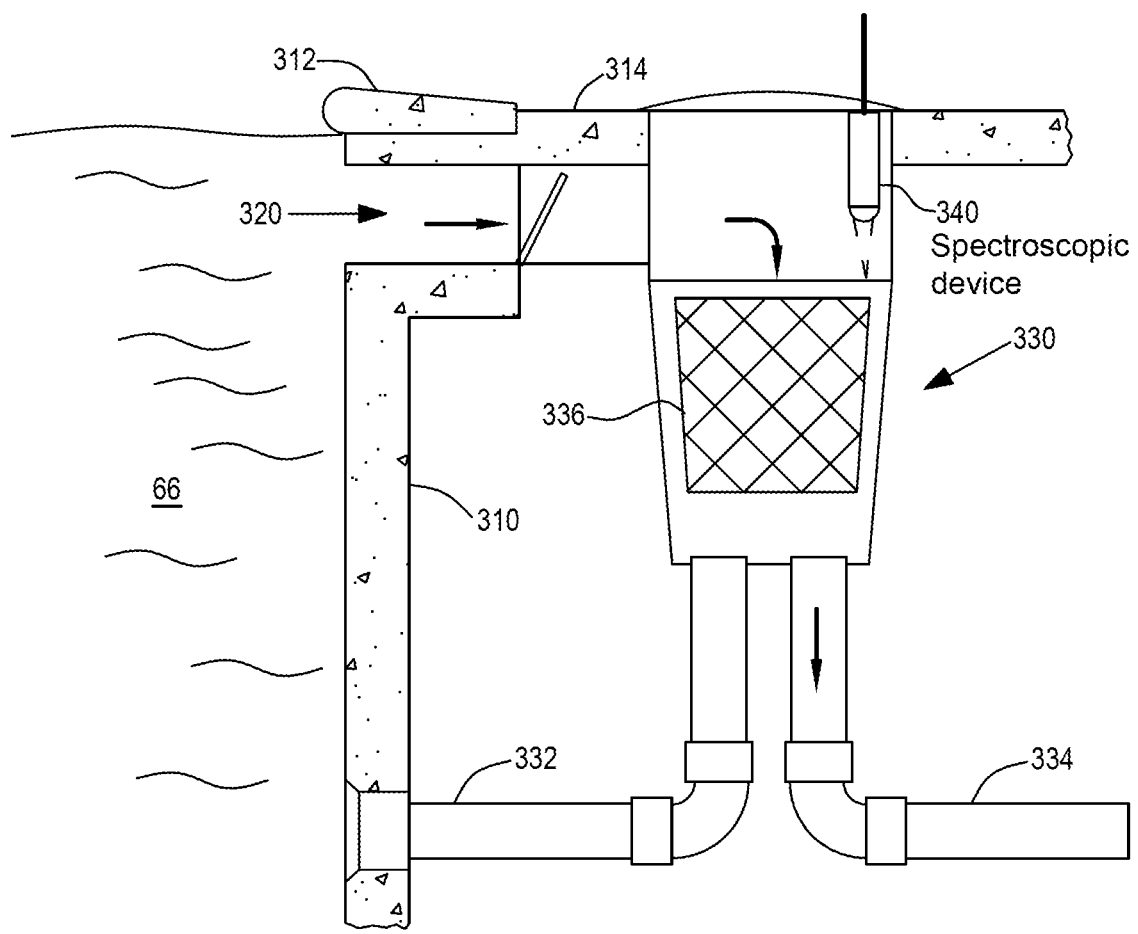
FIG. 9 illustrates a skimmer that includes a spectroscopic device according to an embodiment of the invention.

FIG. 9 illustrates a skimmer 330 and a spectroscopic device according to an embodiment of the invention.

Skimmer 330 includes a skimmer opening 320 for receiving fluid from the pool, filter basket 336, first outlet pipe 332 for supplying fluid that passed through filter 336 to the pool and second pipe 334 for providing pumped fluid to other parts of a pool filtering system such as a main filter.

The skimmer opening is formed in a sidewall 310 of the pool near an edge 312 and upper surface or pool deck 314 surrounding the pool.

Figure 10:
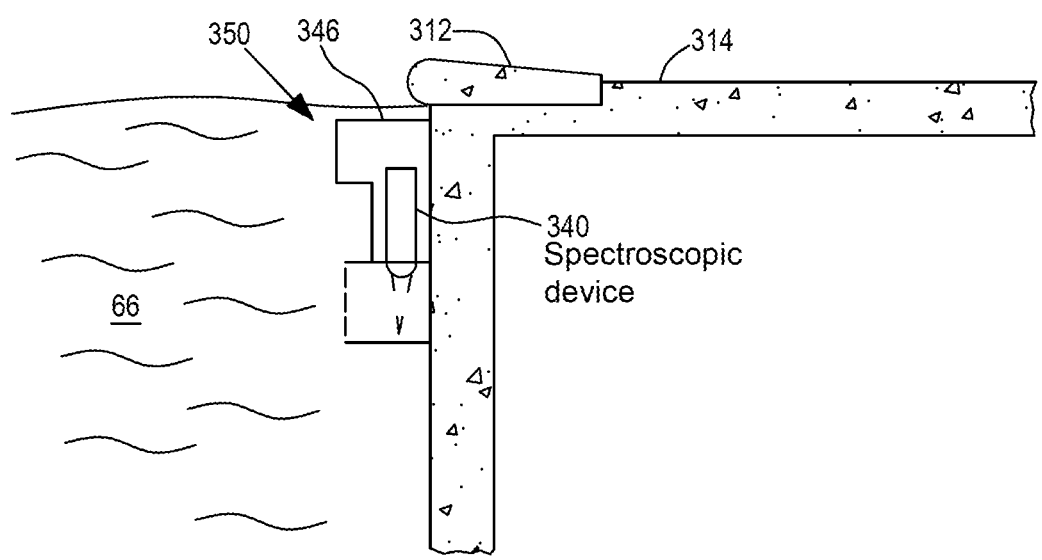
FIG. 10 illustrates a system that is attached to a sidewall of a pool and includes a spectroscopic device according to an embodiment of the invention.
Figure 11:
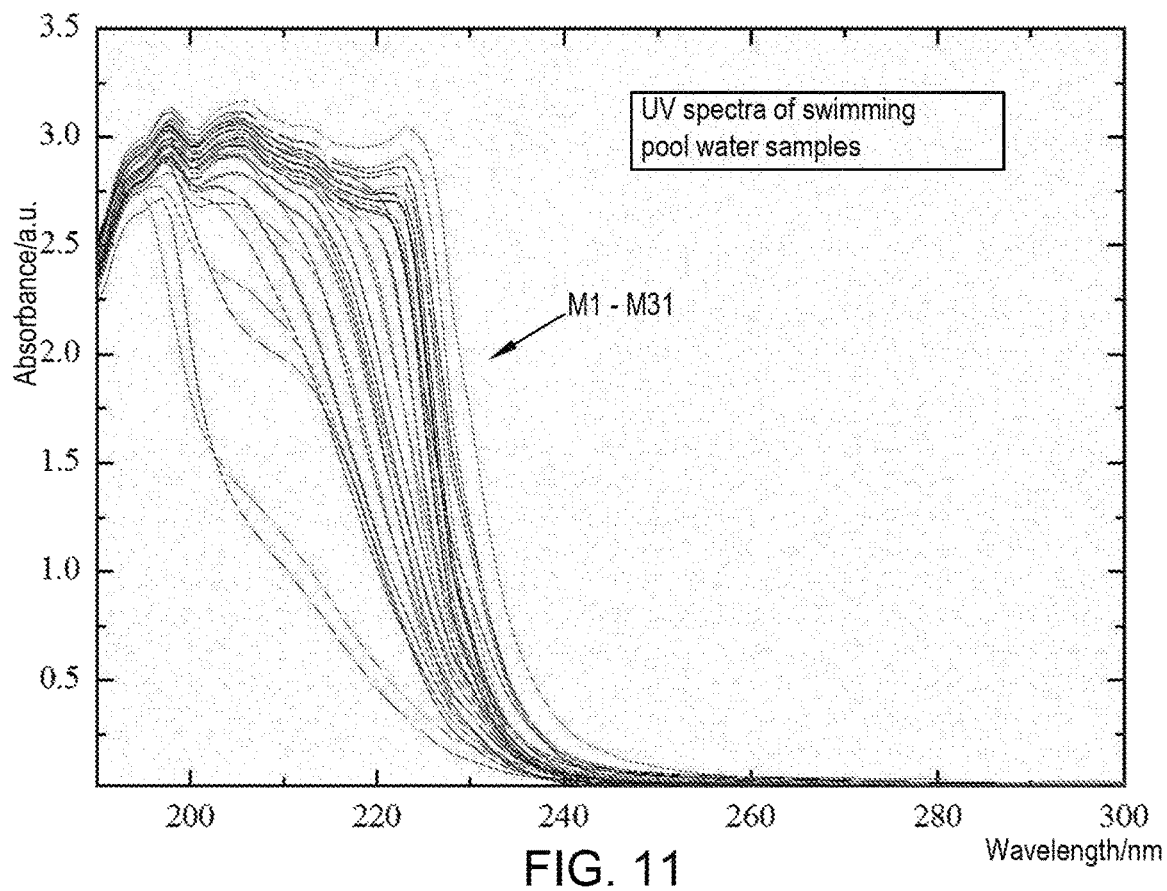
FIGS. 11-15 illustrate fluid samples spectroscopic fingerprints according to an embodiment of the invention.
Figure 12:
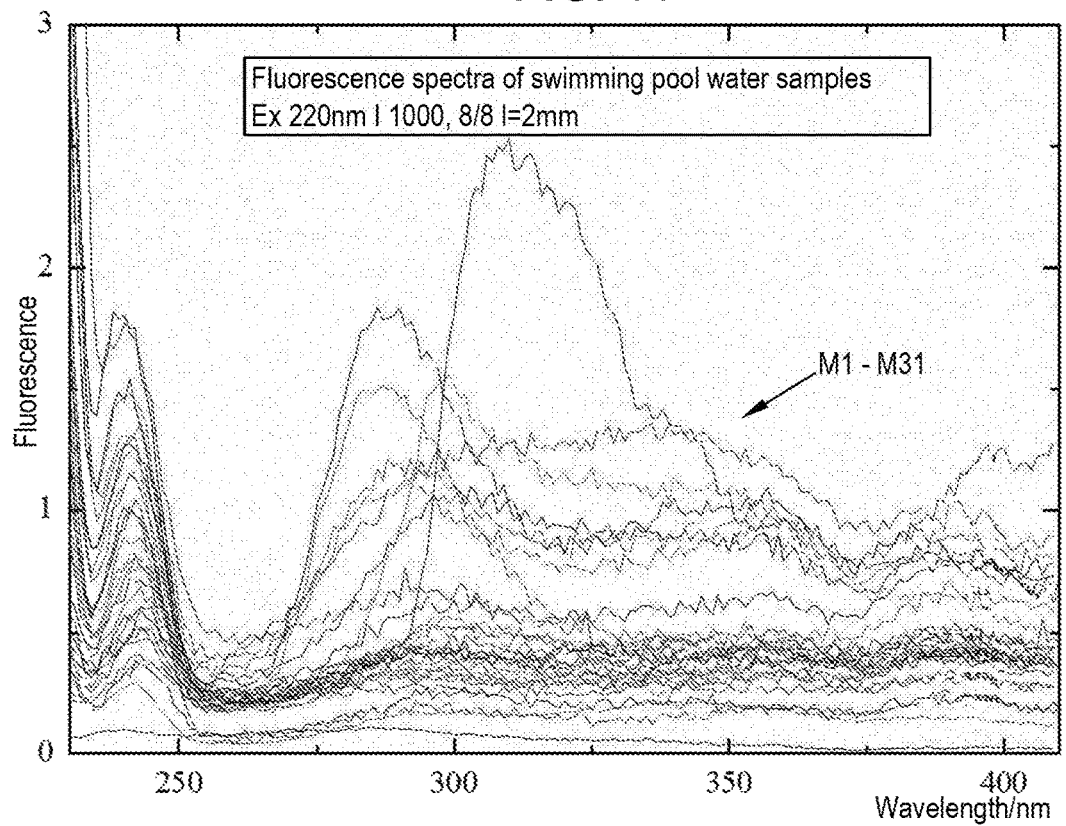
Figure 13:
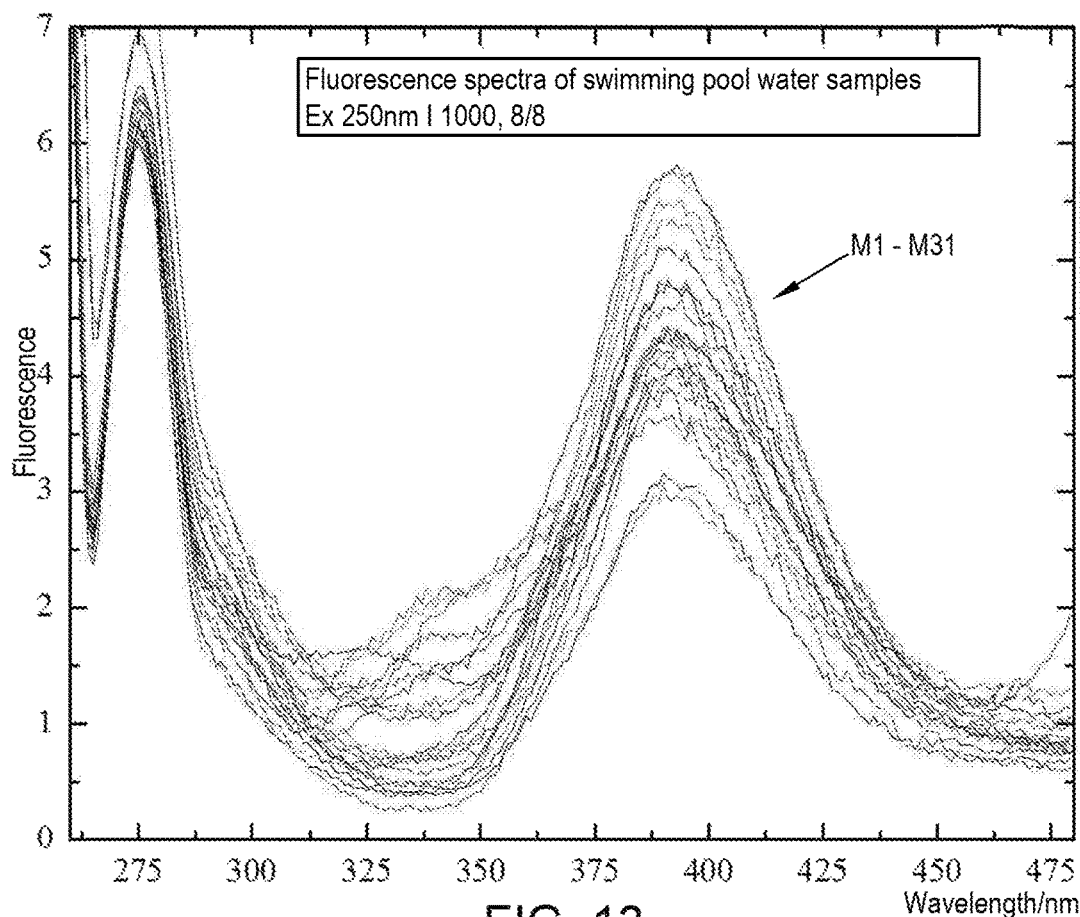
Figure 14:
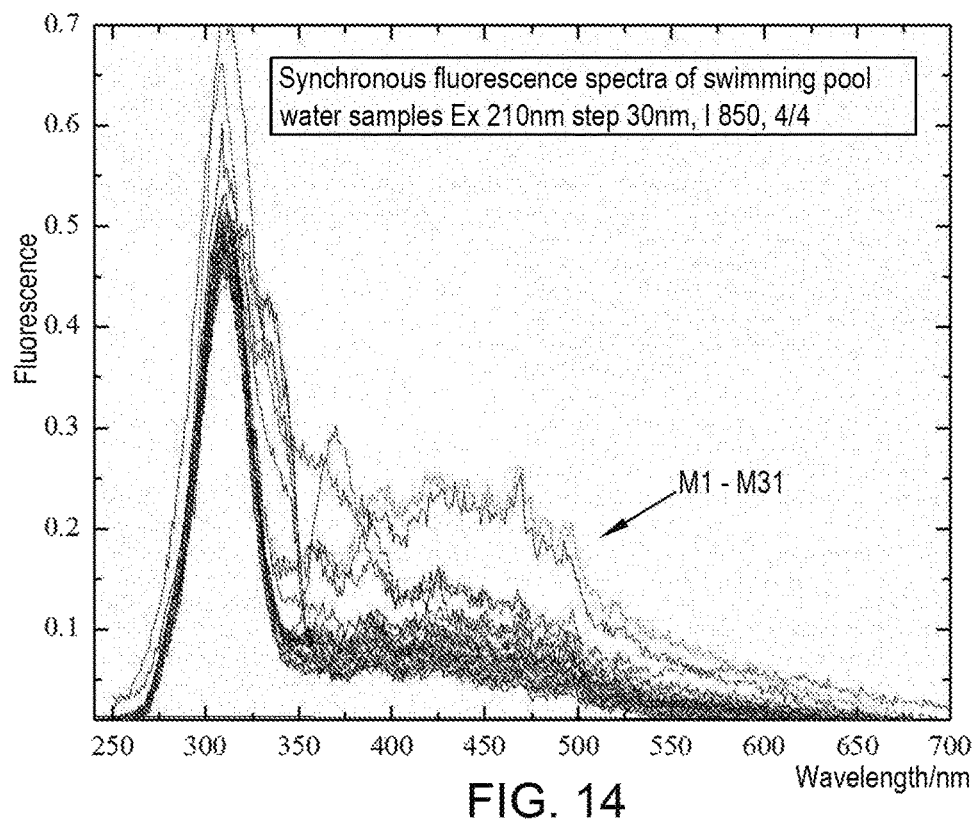
Figure 15:
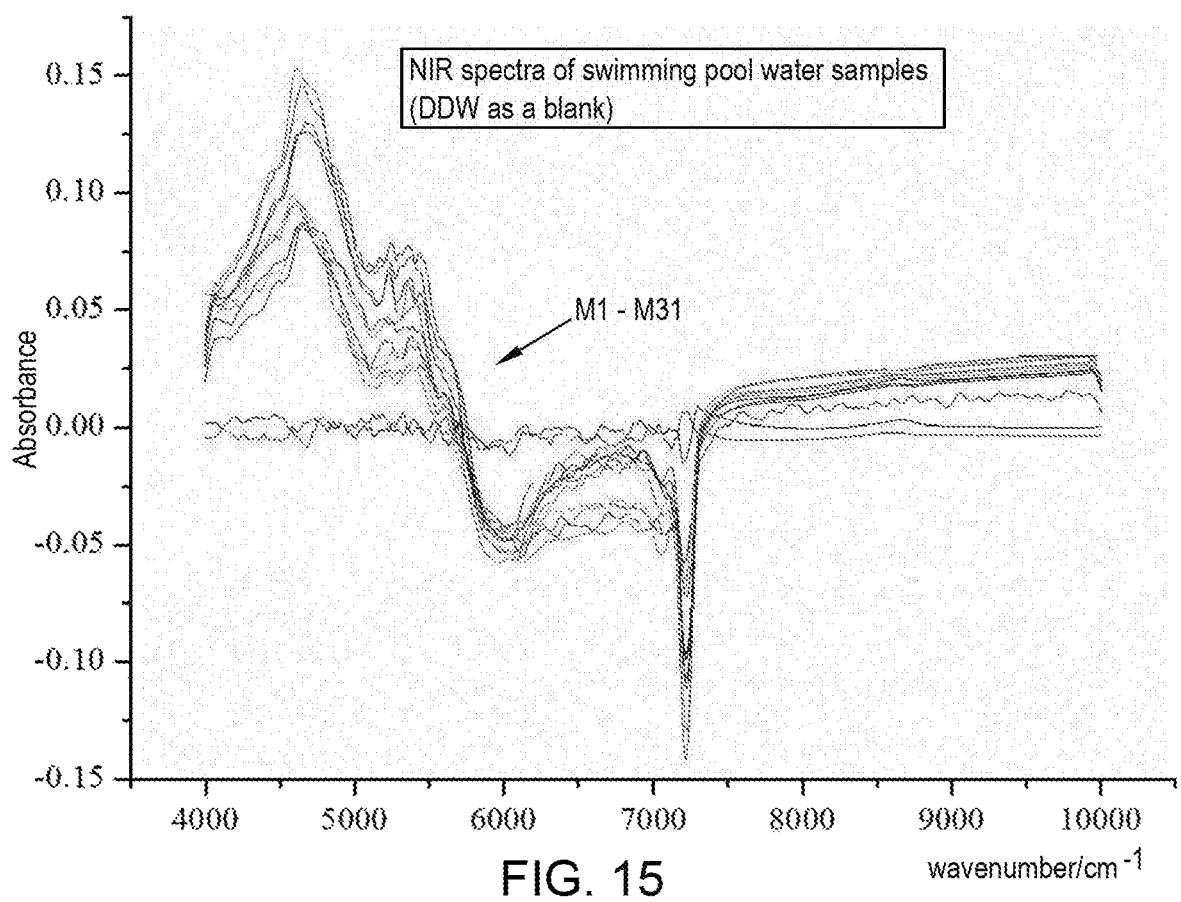
Figure 16:
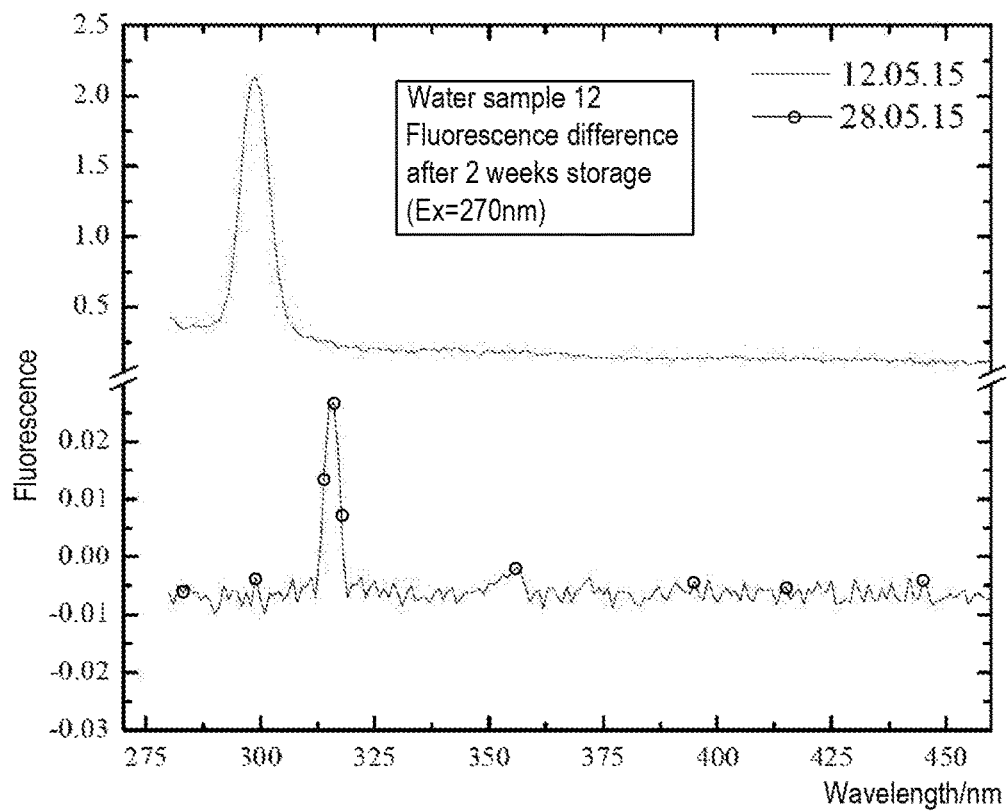
Figure 17:
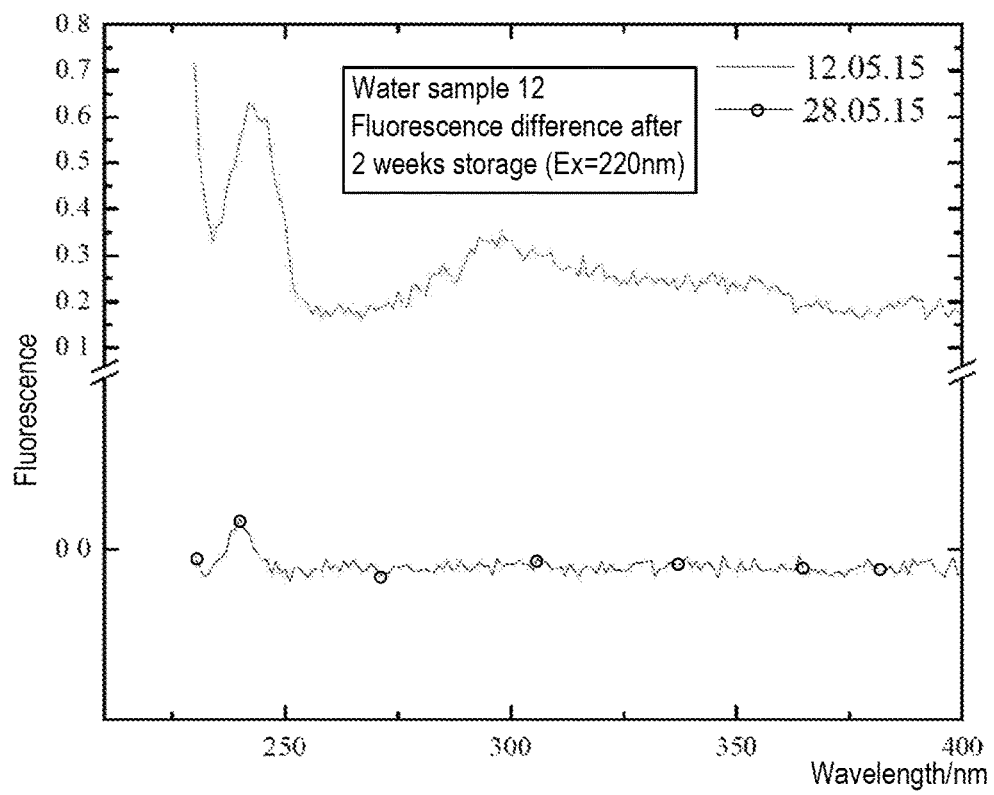
Figure 18:
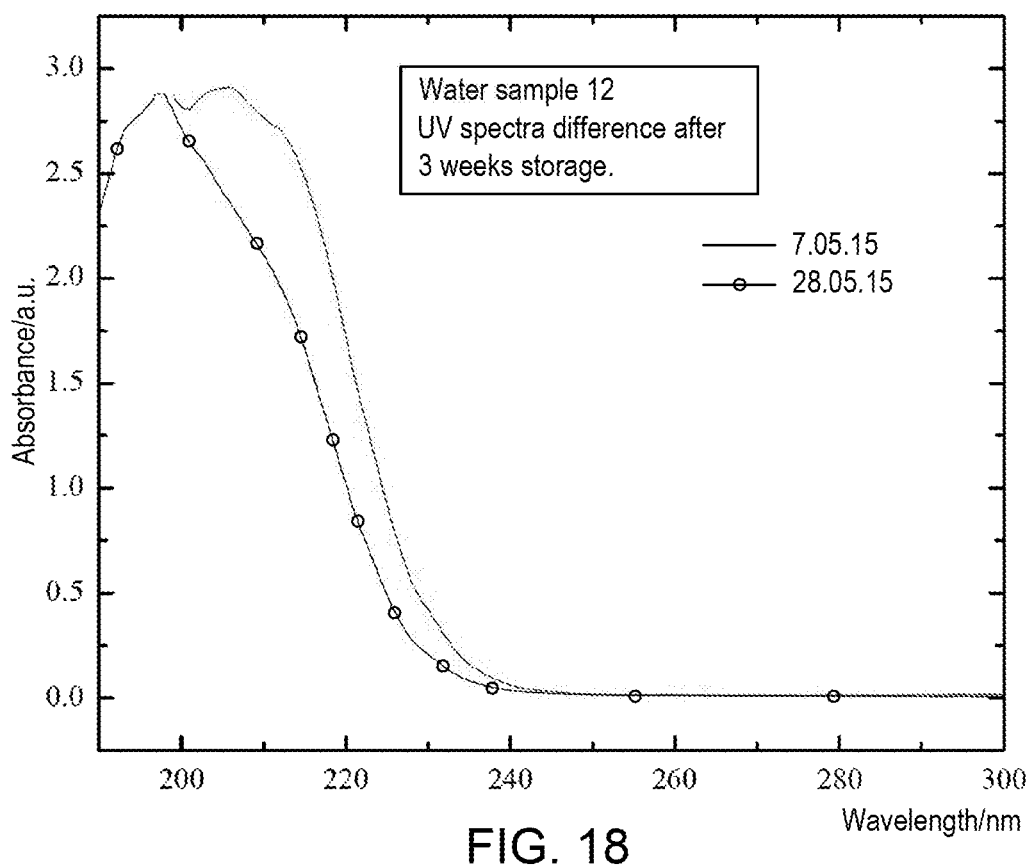
Figure 19:
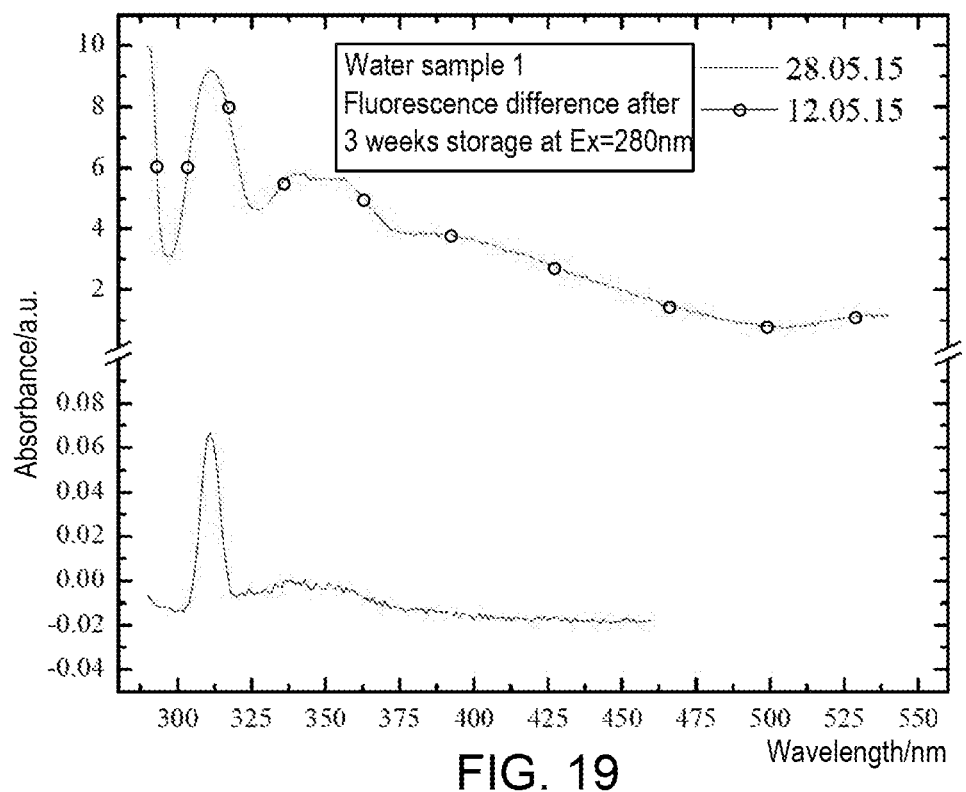
Figure 20:
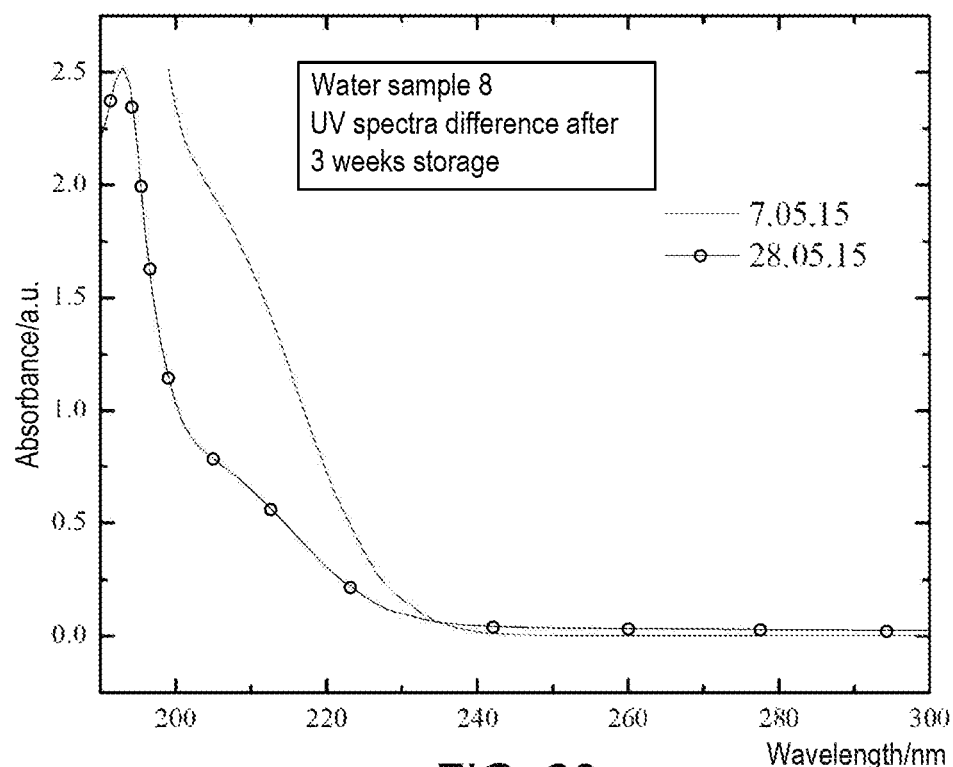
Figure 21:
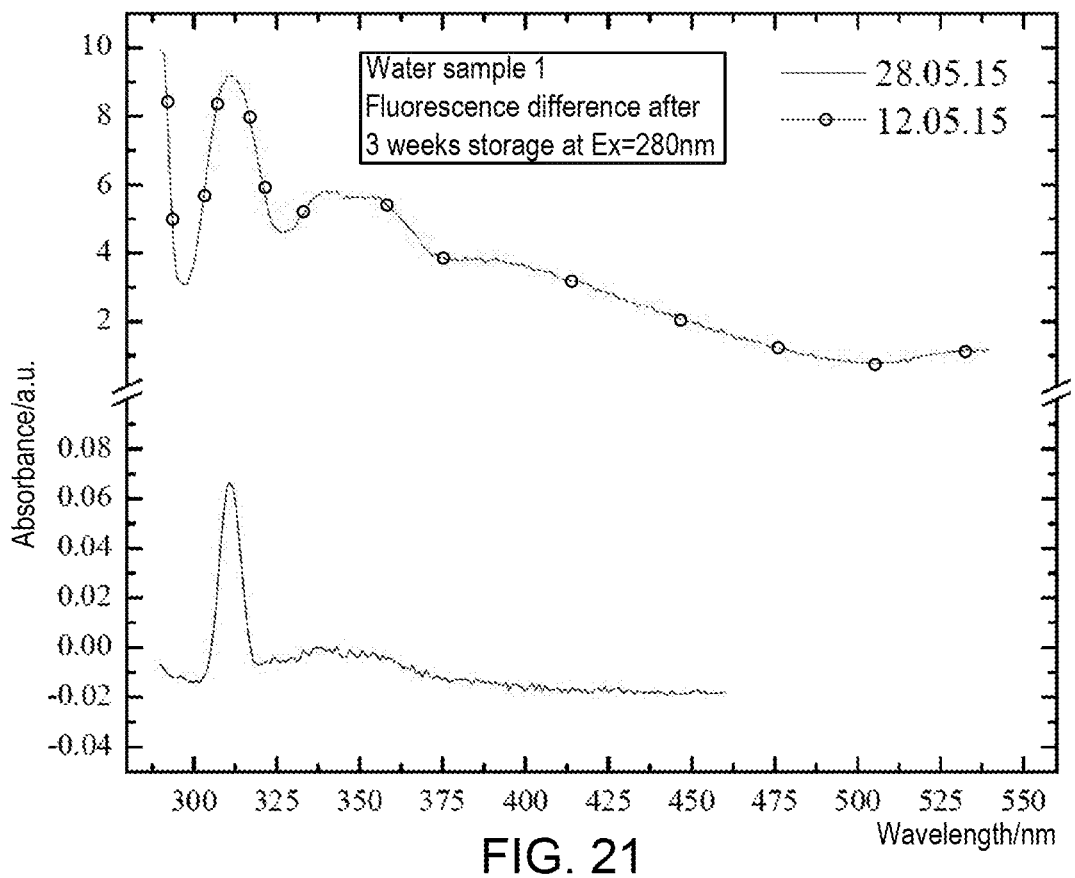
Figure 22:
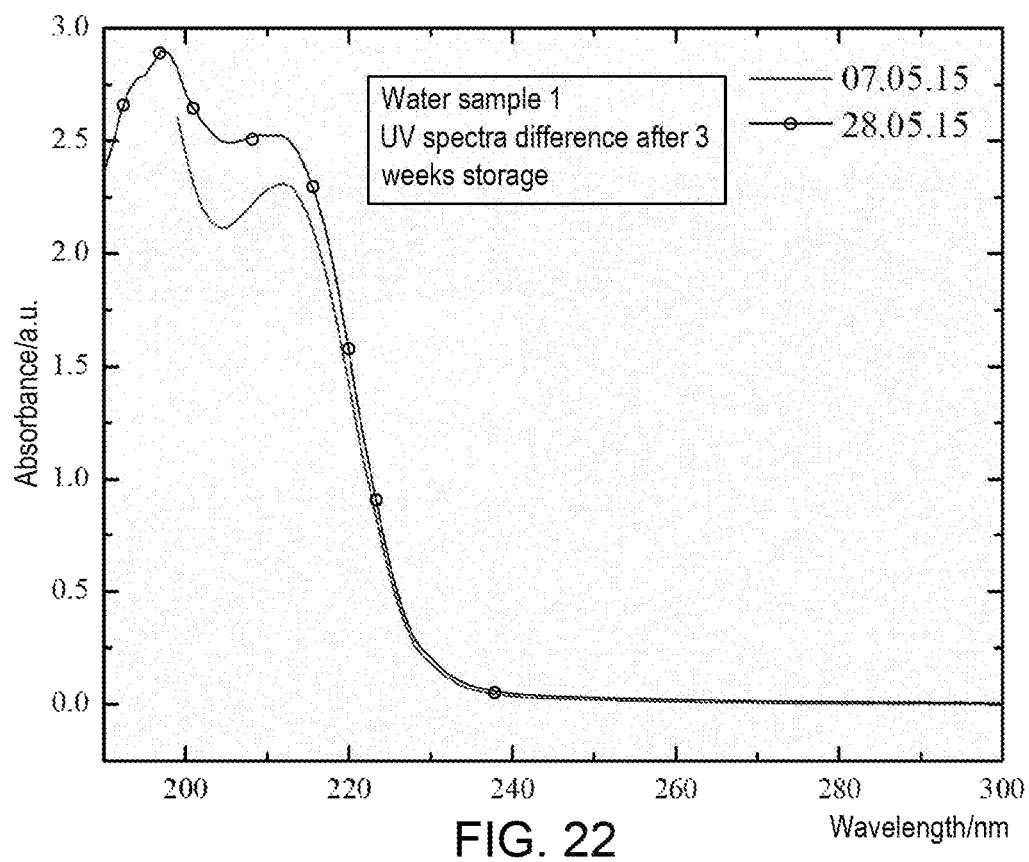

FIG. 10 illustrates a system 350 that is attached (by interface 346) to a sidewall of a pool and includes a spectroscopic device 340 with a communication antenna from the PCB (not shown) according to an embodiment of the invention.

Interface 346 may detachably or non-detachably connect the spectroscopic device 340 to the sidewall of the pool and contain a PCB and a PCB communication antenna (not shown)

According to an embodiment of the invention the spectroscopic device (with or without one or more additional sensor) may be configured to calculate at least one of the following fluid quality parameters: (a) Free available chlorine: Hypochlorous acid (HOCl) plus hypochlorite ion (OCl—) for example—within a relevant concentration range of 0.1-10 parts per million (ppm), (b) combined available chlorine: Chloramines or compounds formed when free chlorine reacts with organic nitrogen-containing compounds. (NH2Cl, NHCl2, NCl3), (c) Total Chlorine: free available chlorine plus combined available chlorine. For example—the relevant concentration range may be 0.1-3 ppm, (d) Cyanuric Acid. For example—the relevant concentration range may be 10-150 ppm, (e) Salinity: total dissolved salts. For example—the relevant concentration range may be up to 5000 ppm, (f) Alkalinity: Bicarbonate. For example—the relevant concentration range may be 20-500 ppm, (g) pH, (h) Turbidity, (i) common contaminants.

Non-limiting examples of common contaminants that can be detected by the system may include: (a) contamination from pool users, including bodily excretions, lotions, sunscreens, cosmetics, etc. These materials include parabens, N,N-diethyl-meta-toluamide (DEET), caffeine and tris(2-carboxyethyl)phosphine (TCEP), (b) contamination from the source fluid used, including humic acids, chlorophyll a, metabolites of aqueous organisms, aliphatic hydroxy acids, aromatic carboxylic acids and some inorganic compounds as bromates, (c) contamination from reactions between disinfectants and the organic components, known as disinfection byproducts (DBPs). There are over 700 DBPs that have been identified in disinfected fluids e.g. trihalomethanes, haloacetic acids, etc, (d) Viruses, bacteria and protozoa in pool fluid are of considerable concern. Viruses relevant to swimming pools include: Adenovirus, Hepatitis A virus (HAV), Echovirus and Norwalk virus. Bacteria which have been linked to swimming pool related disease include: *Mycobacterium marinum, Mycobacterium avium, Pseudomonas aeruginosa, Escherichia coli, Legionella* spp. and *Leptospira interrogans*. Protozoa relevant to swimming pools include *Cryptosporidium parvum, Giardia lamblia, Naegleria* spp. and *Acanthamoeba* spp., (e) Suspended particulates.

The suspended particulates include inorganic particulates, organic particulates and particulates of biological nature. The size distribution might be very wide, starting with nanoparticles and up to microparticles. Currently, the particulates in swimming pools are characterized by the turbidity, which definitely not a sufficient parameter.

FIGS. 11-15 illustrate unique swimming pool fluid sample fingerprints using each spectroscopic method. Each swimming pool has a unique physico-chemo-biological fingerprint, this fingerprint can be determined via optical spectroscopy according to the invention described herein. The spectroscopic results from this set of pools imply that the spectral data can be used as a fingerprinting tool. Almost all samples had significant changes in their UV absorption and fluorescence spectra. This might imply that a chemometric analysis of the spectra can characterize the individual condition of the pools. Nevertheless, it is well known that the performance and reliability of multivariate analysis algorithms is the best when the training set (the set of data used for finding the hidden correlations) is large.

FIGS. 16-22 illustrate results of kinetic measurements that were performed in order to check the stability of the fluid kept in the refrigerator. The results indicate significant spectral changes that take place over a period of weeks. We performed a simple kinetic study, in order to find out how stable the fluid samples are. The samples from the swimming pools were stored in a refrigerator and tested again after a few weeks. We observed considerable changes in all spectral parameters, which means that the samples underwent considerable deterioration with time. We do not have full kinetic data, however, we cannot exclude the possibility that considerable changes take place within days (if not hours). Since the chemical analyses of the samples and the various spectroscopic measurements were performed at different times, they might refer to different conditions of the samples. At the moment, we do not know how severe this effect might be, but our impression is that the changes that take place within a day are tolerable. A more detailed kinetic investigation is recommended, in order to make sure that the correct spectra are being correlated to the actual swimming pool conditions.

Figure 23:
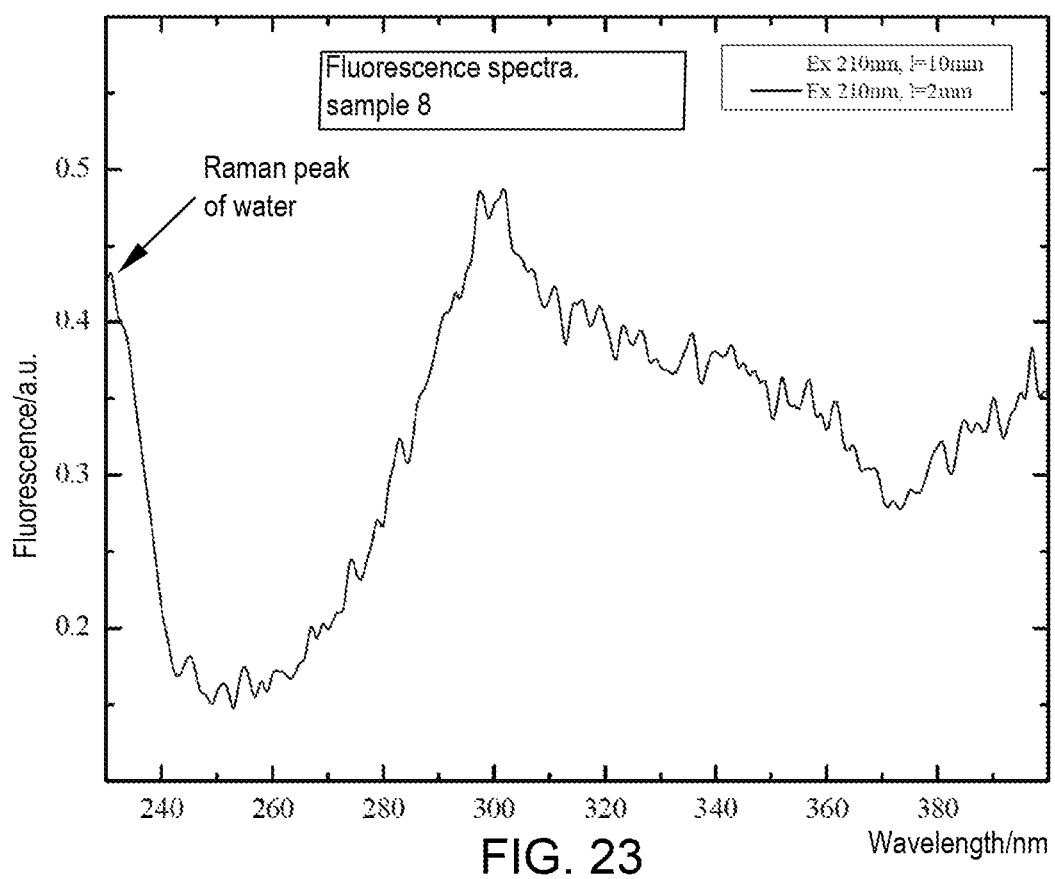
Figure 24:
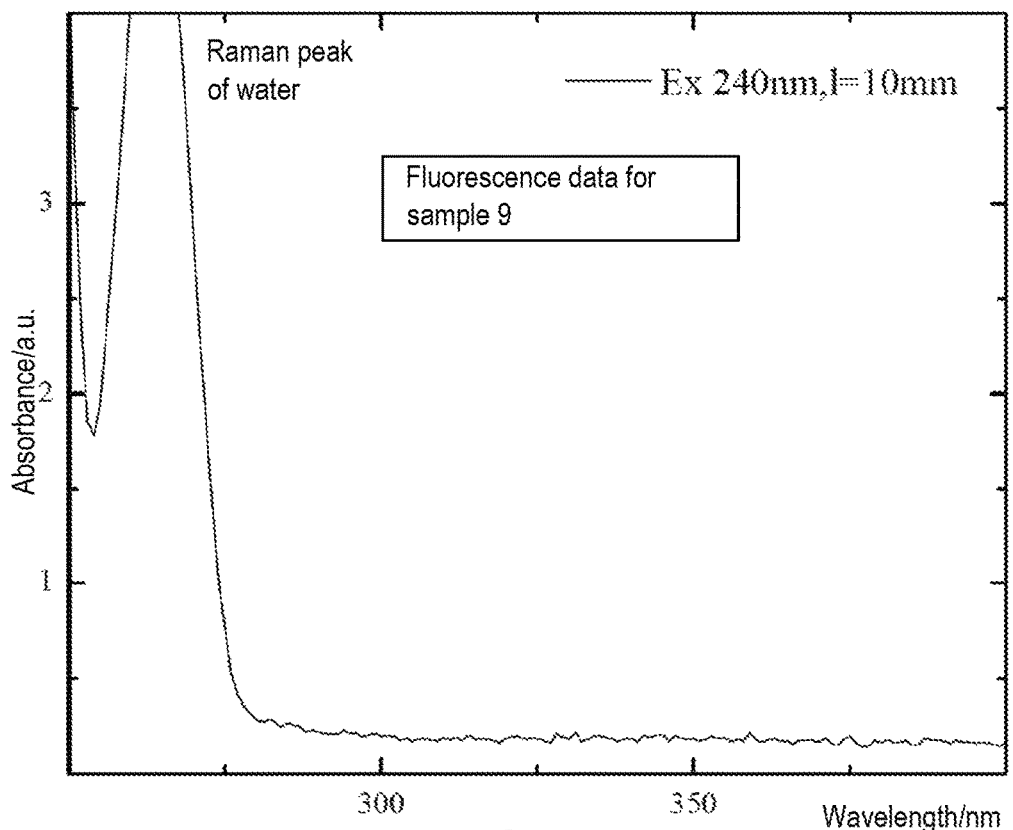

FIGS. 23-24 illustrate fluorescence excitation—an emission Matrix spectroscopy combined with parallel factor analysis was employed to monitor fluid quality and organic contamination in swimming pools. The fluorescence signal of the swimming pool organic matter was low but increased slightly through the day. The analysis revealed that the organic matter fluorescence was characterised by five different components, one of which was unique to swimming pool organic matter and one which was specific to organic contamination. The latter component had emission peaks at 420 nm and was found to be a sensitive indicator of organic loading in swimming pool fluid. The fluorescence at 420 nm gradually increased during opening hours and represented material accumulating through the day.

Figure 25:
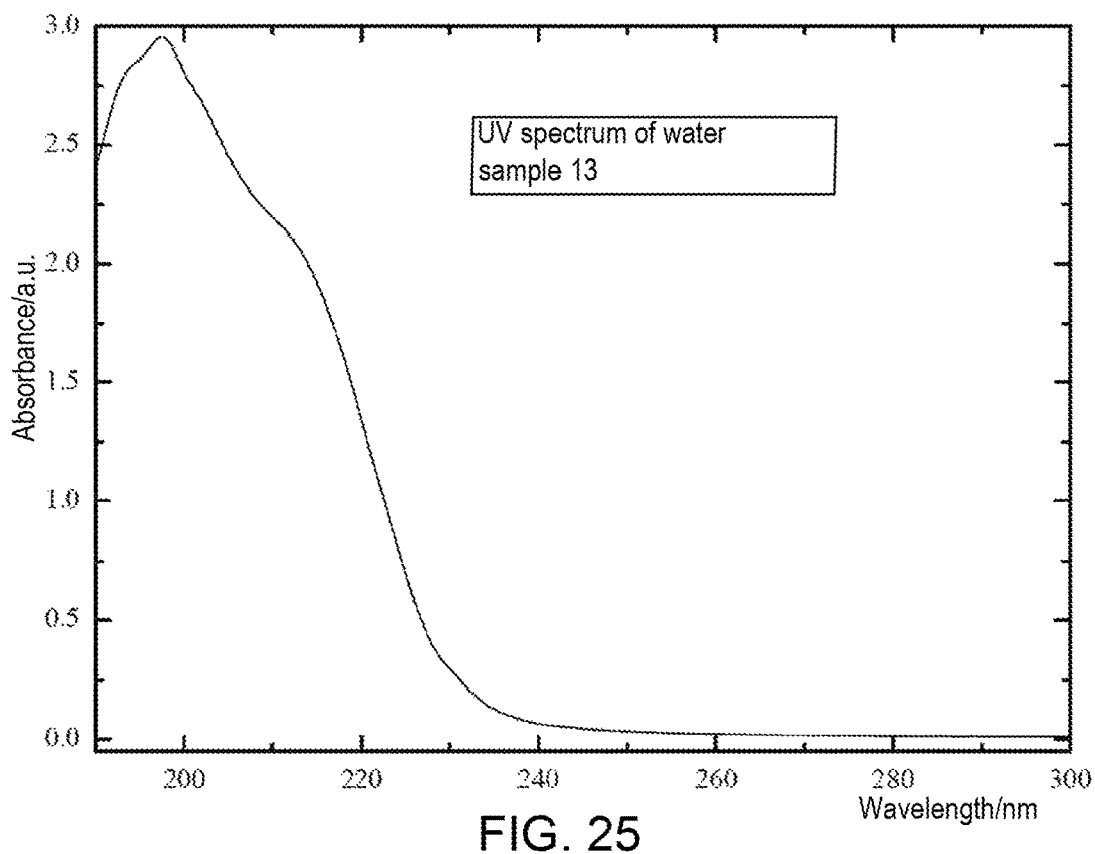
Figure 26:
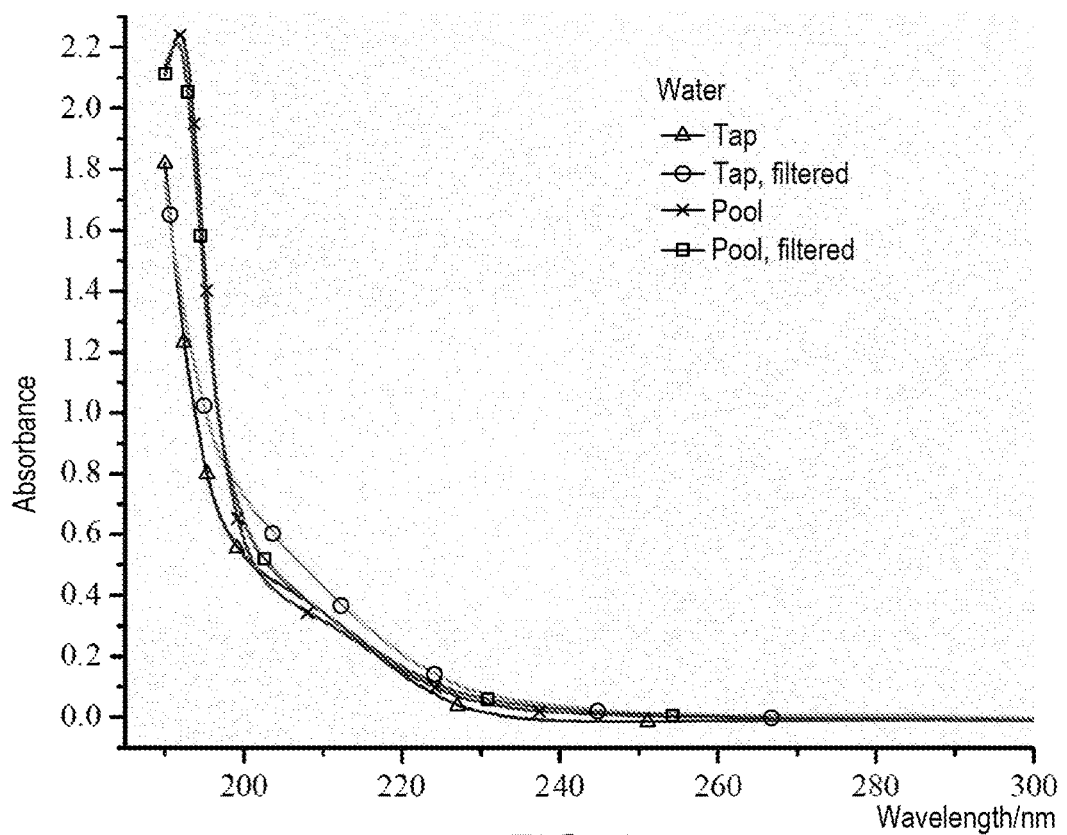
Figure 27:
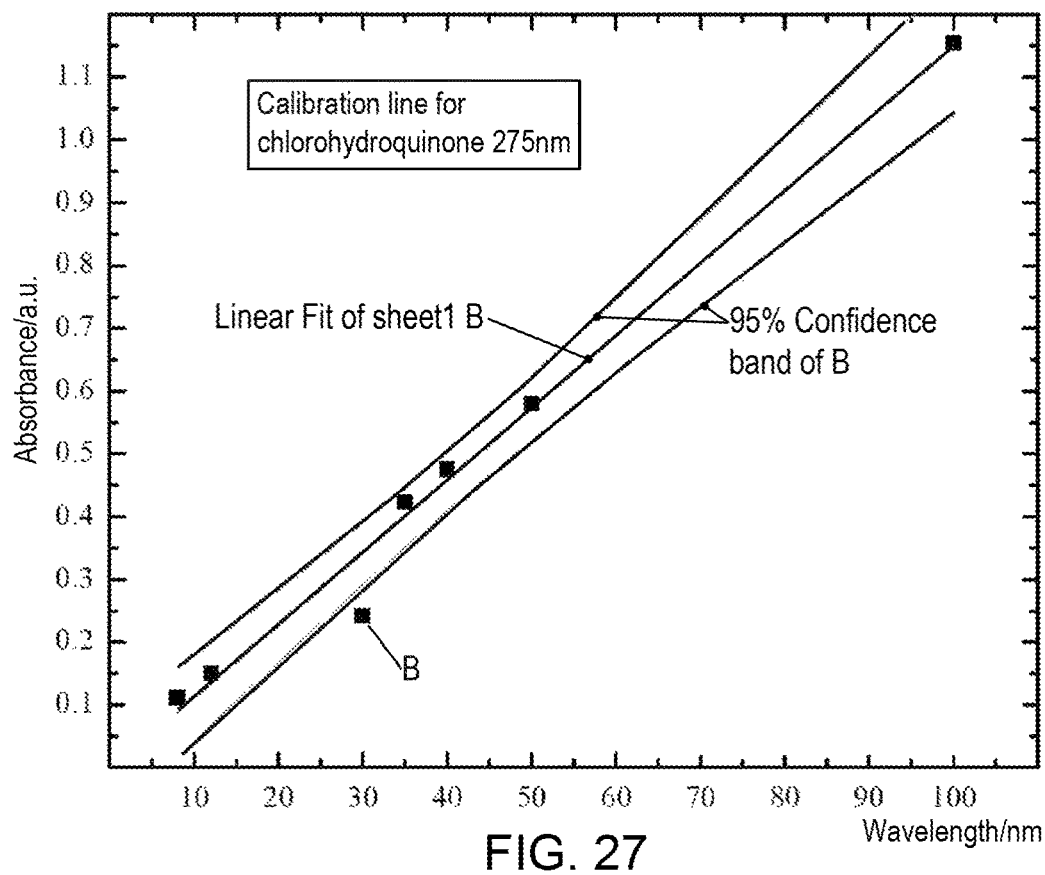
Figure 28:
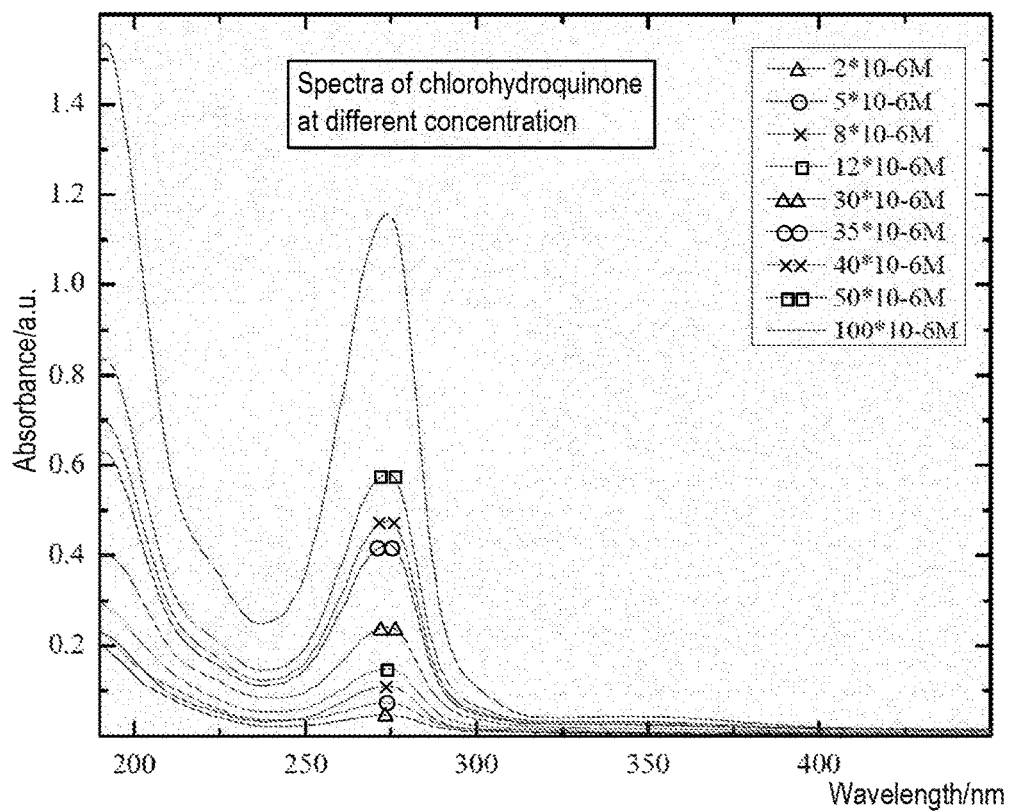
Figure 29:
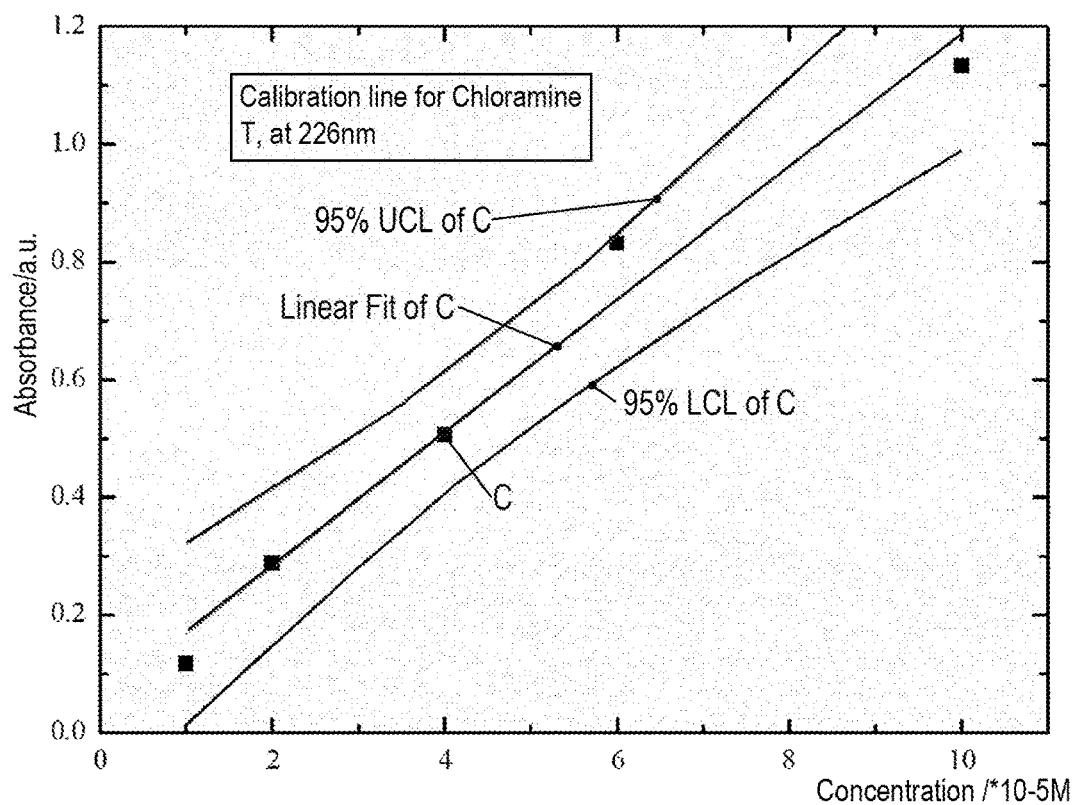
Figure 30:
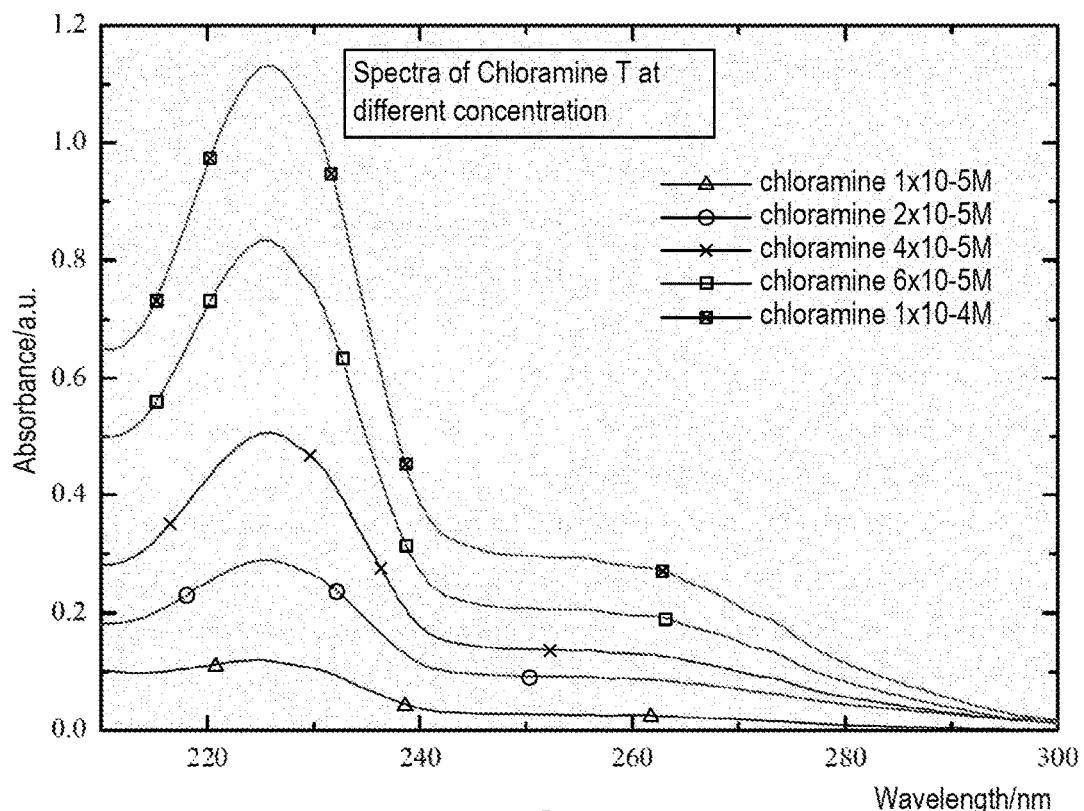

FIGS. 25-26 illustrate a comparison between the UV absorption of a swimming pool samples to that of tap fluid. The measurements were repeated for both samples after filtration (0.45 micron). The results are shown. All tested swimming pool fluids exhibited a stronger characteristic absorption at about 195 nm, which is different from that of tap fluid. The filtration had an observable effect on the absorption spectra, but did not affect the main peak at 195 nm. FIG. 25 illustrate a more detailed spectrum of a characteristic swimming pool sample is shown. It indicates a clear peak at 195 nm and a shoulder at 215 nm.

FIGS. 27-30 are Quantification plots of some relevant compound were obtained, in order to estimate the method sensitivity. For some of the compounds, quantification plots have been measured, in order to test the sensitivities. The quantification plots imply that the sensitivities might be adequate for measurement of the tested compounds in the concentration range relevant to swimming pools.

Figure 31:
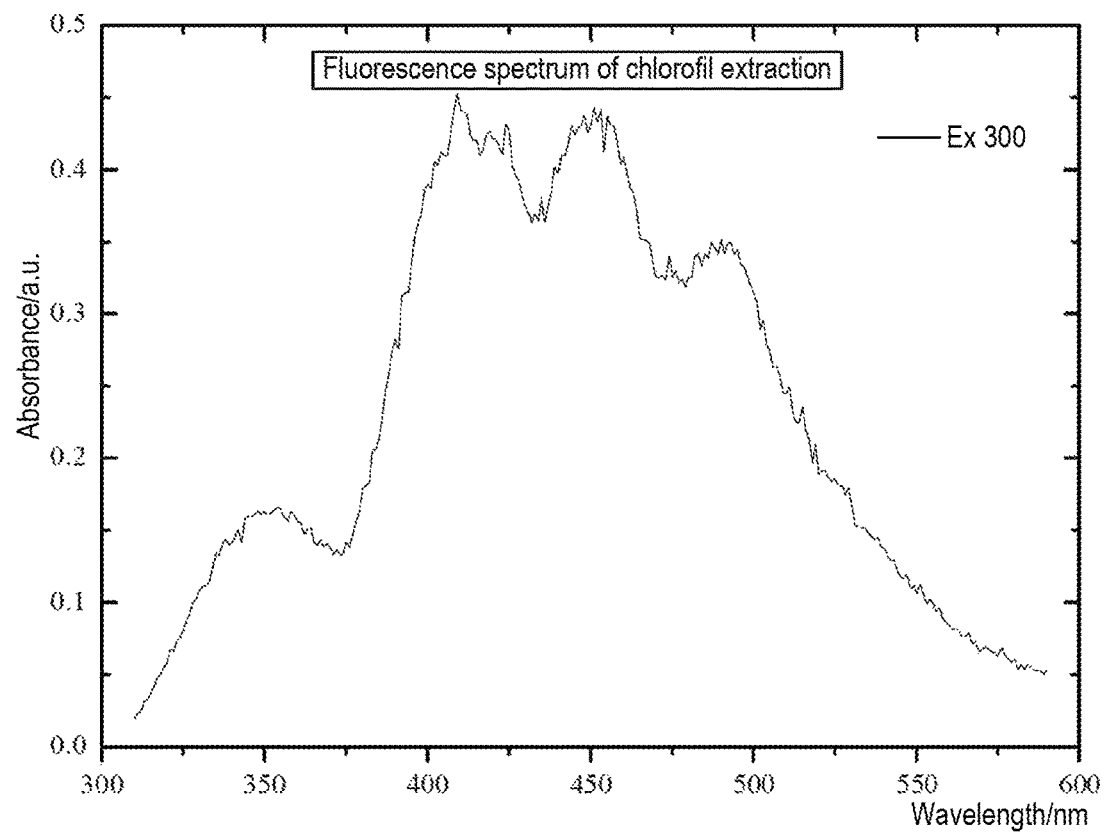
Figure 32:
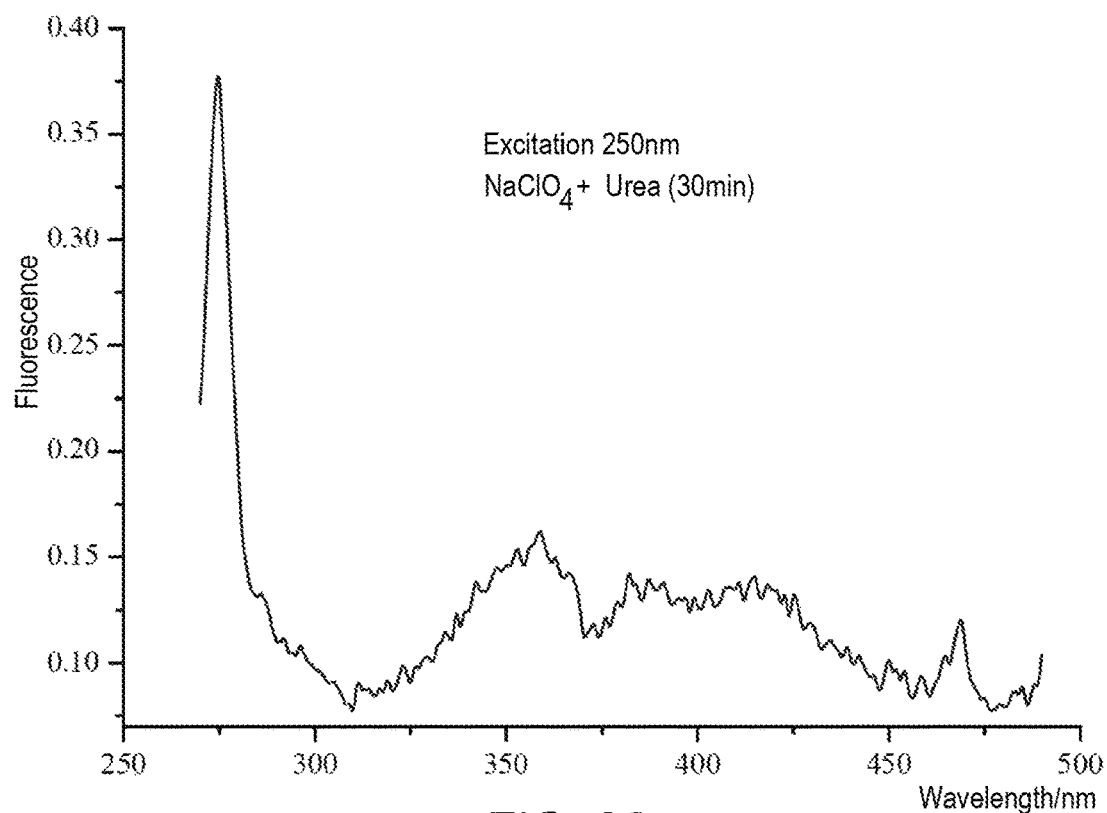
Figure 33:
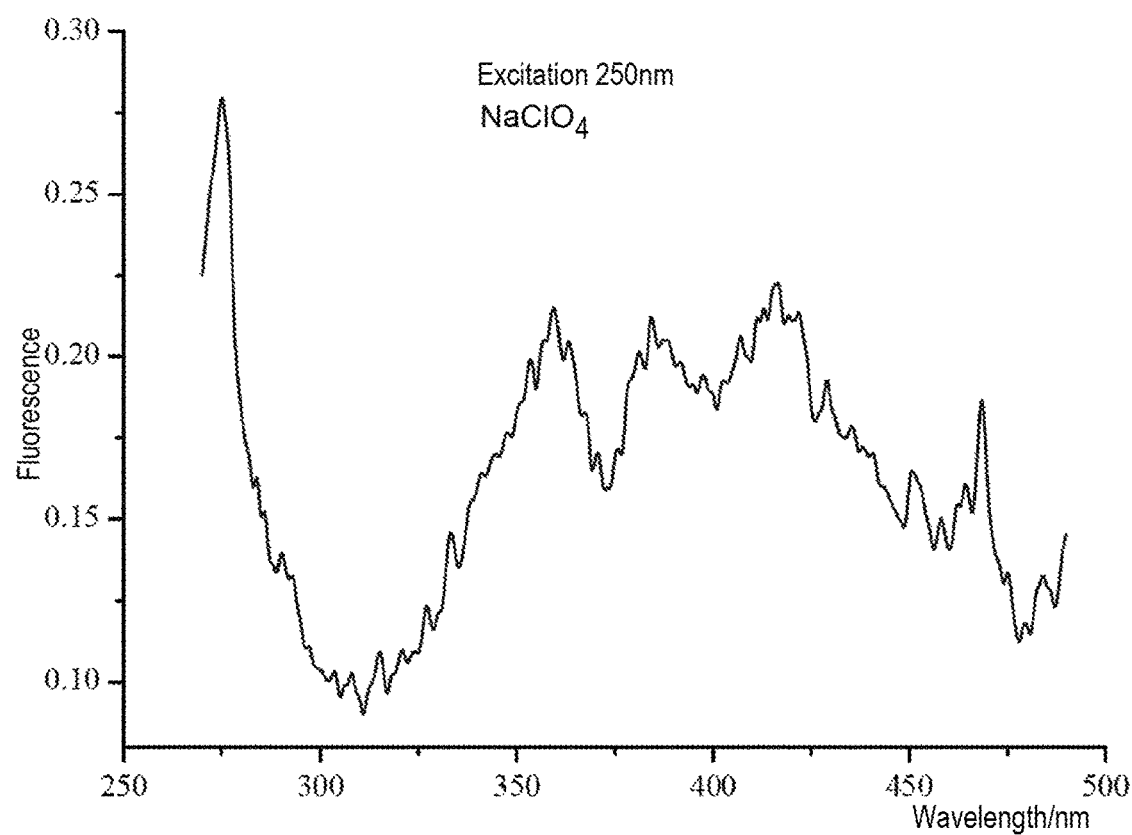
Figure 34:
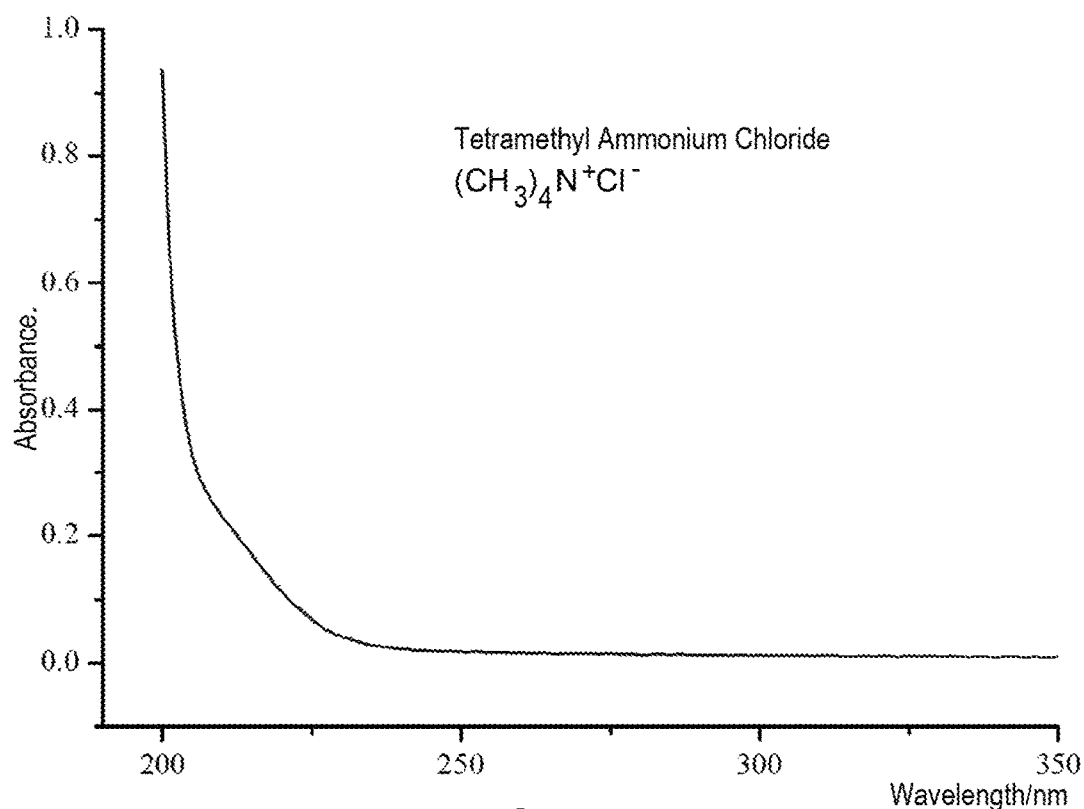
Figure 35:
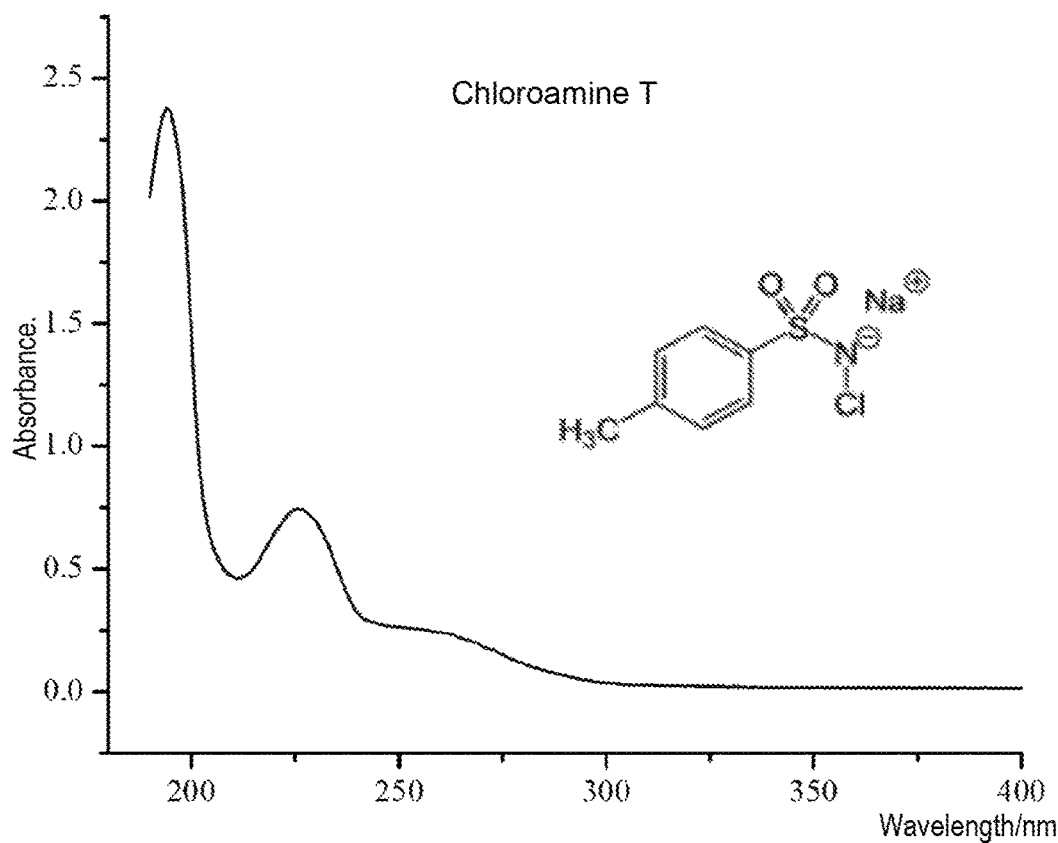
Figure 36:
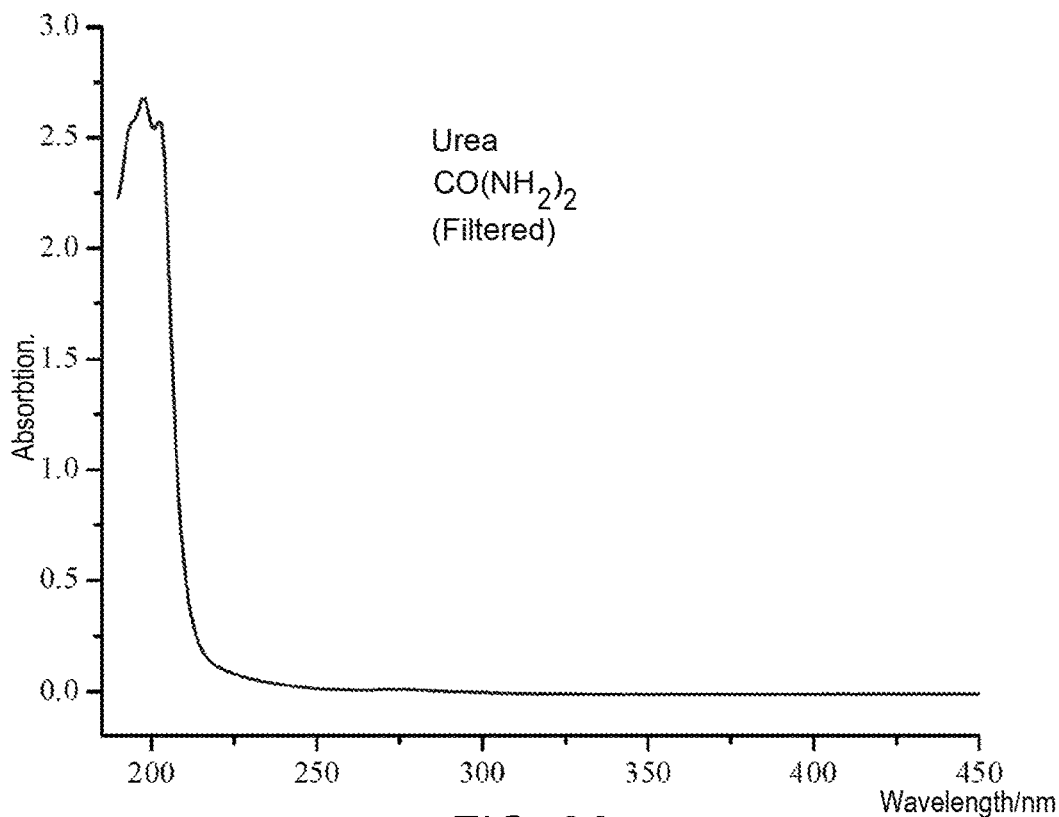
Figure 37:
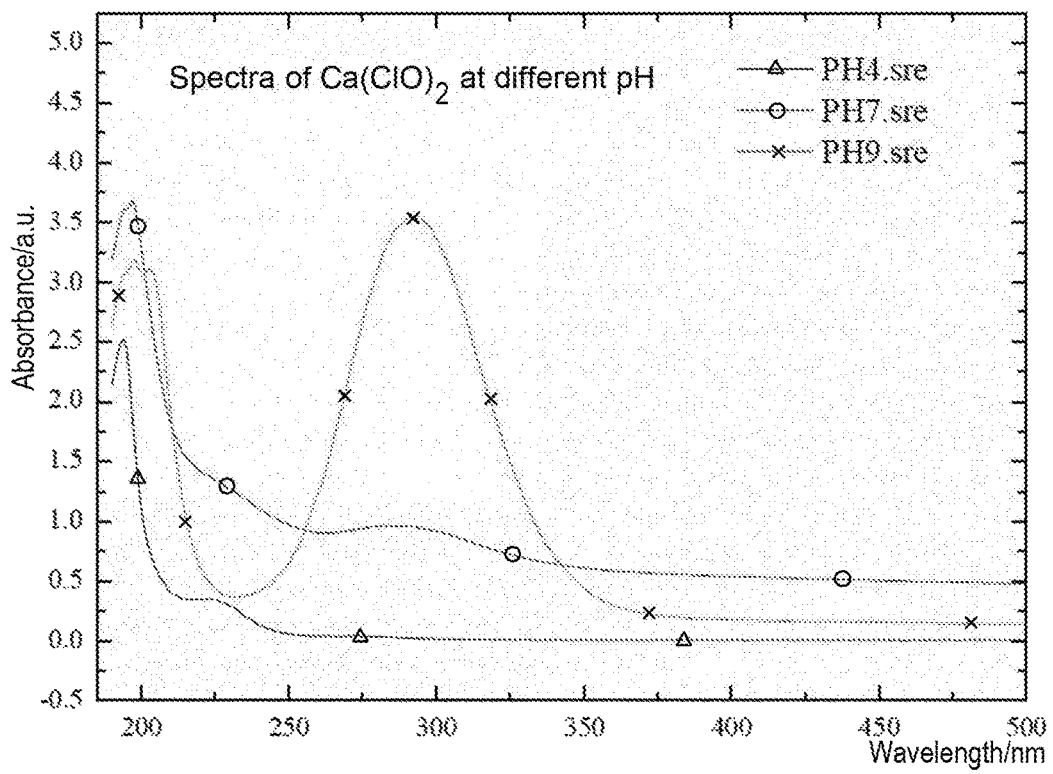

FIGS. 31-33 provide an example of the fluorescence emitted by NaClO4 solution, when excited at 250 nm wavelength is shown. The by-products obtained under natural swimming pool conditions were mimicked by adding urea and waiting for half an hour. The thus obtained fluorescence spectrum is shown.

FIGS. 34-38 provide an example of Spectral measurements in DDW. UV Absorption. We first measured the UV absorption of DDW and of filtered (0.45 µm) tap fluid. The results are shown. We also measured the UV absorption of a variety of compounds in DDW. The compounds were selected according to their relevance to swimming pools. They are either known contaminants or represent known contaminants. The results are shown.

Figures 38, 39:
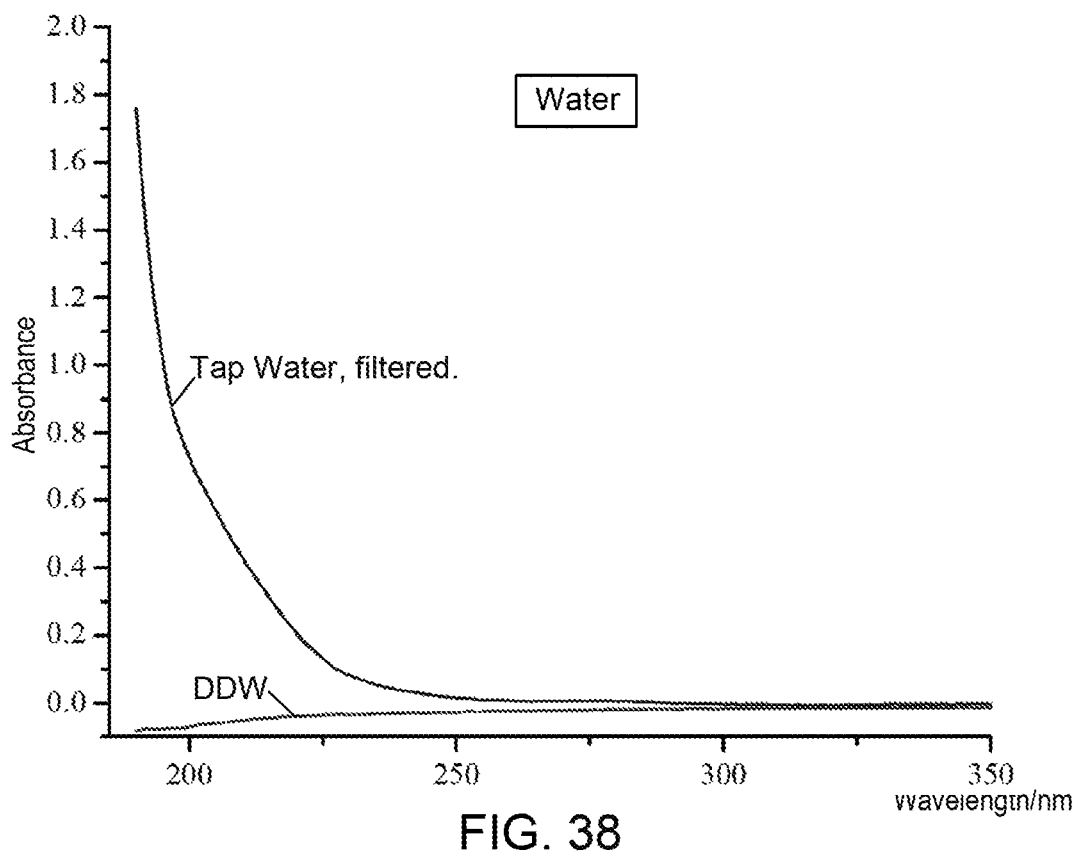

FIG. 39 illustrates a parallel factor analysis (PARAFAC) modeling of the swimming pool samples, including samples with and without wastefluid addition revealed that the fluorescence of organic matter in swimming pools could be characterized by five different fluorescence components. These are shown in the following Table: Component 5 was unique to swimming pool organic matter, exhibiting excitation maximum at <240 and 310 nm and emission maximum at 360 nm. Component 3 was a very good indicator for anthropogenic release to swimming pool fluid. It exhibited emission maximum at 420 and had two excitation peaks: one below 240 and the other at 330 nm.

FIGS. 40-41 illustrate state when chlorine is added to fluid, dissolved chlorine (Cl2), Hypochlorous acid (HOCl) and the hypochlorite ion (OCl—) are produced. The balance between these species depends on the fluid pH and on temperature. At pH values lower than 3 most of the chlorine is in the form of dissolved gas (Cl2), at pH values around 5 chlorine mainly exists in the form of HOCl, and is converted to the OCl— form if the pH is increased to 9 or higher. Therefore, by controlling the pH the UV absorption spectra of these species were measured. The hypochlorite ion (OCl—) ion has the strongest molar absorption coefficient and has its absorption peak centered around 290 nm. The peak of dissolved Cl2 is at 229 nm and of HOCl at 233 nm. The absorption measurement at 290 nm is far less affected by the presence of nitrite and nitrate ions, which are common in natural fluids, with their large absorption peaks centered at 203 and 210 nm. The UV absorption spectra of the above species are shown.

Figure 42:
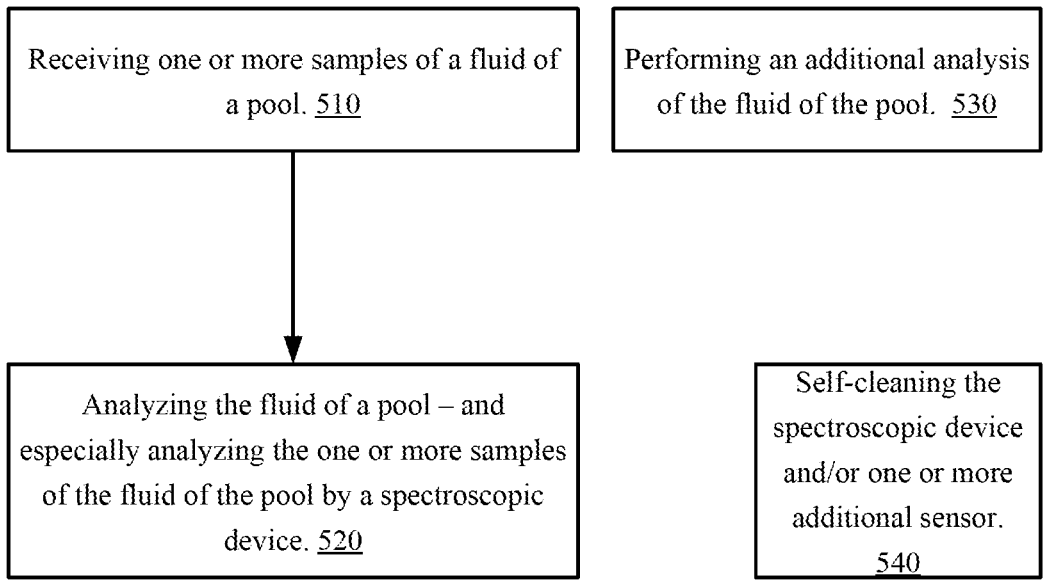
FIG. 42 illustrates a method according to an embodiment of the invention.

FIG. 42 illustrates method 500 according to an embodiment of the invention.

Method 500 may be executed by any system illustrated above.

Method 500 may include step 510 of receiving one or more samples of a fluid of a pool.

Step 510 may be followed by step 520 of analyzing the fluid of a pool—and especially analyzing the one or more samples of the fluid of the pool by a spectroscopic device.

Step 520 may include applying any number of spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (g) fluorescence near infrared spectroscopy, and (f) synchronous fluorescence spectroscopy.

Step 520 may include applying a chemometric algorithm.

Step 520 may include analyzing at least two of the following: (a) a wavelength range between one hundred eighty nanometers and two hundred nanometers, (b) one or more sub-region of a wavelength range between one hundred eighty nanometers and two hundred nanometers, (c) a wavelength range between two hundred and sixty nanometers and two hundred and eighty nanometers, (d) one or more sub-region of a wavelength range between two hundred and sixty nanometers and two hundred and eighty nanometers, (e) a wavelength of two hundred and fifty four nanometers, (f) a wavelength range between nine hundred eighty nanometers and one thousand nanometers, (g) one or more sub-region of a wavelength range between nine hundred eighty nanometers and one thousand nanometers, (h) a wavelength range between one thousand two hundred and sixty nanometers and one thousand two hundred and eighty nanometers, (i) one or more sub-region of a wavelength range between one thousand two hundred and sixty nanometers and one thousand two hundred and eighty nanometers, and (j) a wavelength of one thousand two hundred and fifty four nanometers.

Step 520 may include applying the one or more spectroscopic technique at a resolution of one nanometer, or a resolution that does not exceed one nanometer or a resolution that exceeds one nanometer.

Method 500 may include step 530 of performing an additional analysis of the fluid of the pool. The analysis can be performed on the sampled obtained during step 510 or on other samples. The additional analysis is not a spectroscopic analysis.

Step 530 may include performing the additional analysis by at least one additional sensor out of (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, (m) a Salinity sensor.

Method 500 may also include step 540 of self-cleaning the spectroscopic device and/or one or more additional sensor. Self-cleaning refers to cleaning by the system and not by a human.

The self-cleaning may involve using a self-cleaning mechanism such as but not limited to an acoustic vibrator, a mechanical cleaning element.

Either one of steps 510, 520, 530 and 540 can be executed by a pool cleaning robot, by a system that includes a floating unit and a submerged unit, by a system that is connected to the sidewall of the pool, by a skimmer, by a system that is included within a skimmer, by a system that receives fluid from a pool filtering system, by the pool filtering system.

Step 520 may include directing, by optics, electromagnetic radiation through an opening formed in a pipe and receiving electromagnetic radiation from the fluid.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements the mere fact that certain measures are recited in mutually different claims does not indicate that a combination of these measures cannot be used to advantage.

Any reference to the term "comprising" or "having" should be interpreted also as referring to "consisting" of "essentially consisting of". For example—a system that comprises certain components can include additional components, can be limited to the certain components or may include additional components that do not materially affect the basic and novel characteristics of the system—respectively.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A method for determining values of multiple parameters in swimming-pool fluid, containing chlorine as a disinfectant agent, said method comprising the following steps:
   a. sampling said swimming-pool fluid and obtaining a single spectrometric fingerprint of said swimming-pool fluid either in the visible band or the UV band by a spectroscopic device;
   b. sampling said swimming-pool fluid and obtaining data from at least one additional sensor different from a spectrometric sensor, said at least one additional sensor selected from a pH sensor, an ORP sensor, a temperature sensor, an electrical conductivity sensor, a pressure sensor, ion-selective electrodes, a flow rate sensor, a free Chlorine sensor, a combined Chlorine sensor, a turbidity sensor, a Cyanuric sensor, an Alkalinity sensor, and a Salinity sensor, sending said spectrometric fingerprint and sensor data to a processing unit,
   wherein the single spectrometric fingerprint and the data from the at least one additional sensor are taken at the same time;
   c. analyzing signals generated by said spectroscopic sensor and by said at least one additional sensor via a Chemometric algorithm which includes at least one of the following multivariate calibration techniques, supervised multivariate classification techniques, unsupervised classification techniques, multivariate curve resolution, multivariate statistical process control (MSPC), and multiway methods to provide a swimming pool analysis report and obtain values of quality parameters from said analysis report, said parameters include at least one of a pH level, the concentration of Hypochlorite ions ($OCl^{-1}$), and the concentration of Cyanuric acid in said swimming pool fluid,
   wherein the analysis report is based on the single spectrometric fingerprint and the data from the at least one additional sensor.

2. The method of claim 1, comprising applying at least one spectroscopic technique selected from: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, (g) synchronous fluorescence spectroscopy, and (h) reflectance ultra-violet-visible spectroscopy to provide at least one of a pH level, concentration of Hypochlorite ions ($OCl^{-1}$), and concentrations of Cyanuric acid.

3. The method of claim 1, wherein said at least one additional sensor comprises a turbidity sensor and a temperature sensor.

4. The method of claim 1, wherein said at least one additional sensor comprises a conductivity sensor and a temperature sensor.

5. The method of claim 1, wherein said at least one additional sensor comprises a turbidity sensor and an electrical conductivity sensor.

\* \* \* \* \*